United States Patent
Iliff

(10) Patent No.: US 7,344,496 B2
(45) Date of Patent: *Mar. 18, 2008

(54) COMPUTERIZED MEDICAL DIAGNOSTIC SYSTEM UTILIZING LIST-BASED PROCESSING

(75) Inventor: Edwin C. Iliff, La Jolla, CA (US)

(73) Assignee: Clinical Decision Support, LLC, Nashville, TN (US)

(*) Notice: Subject to any disclaimer, the term of this patent is extended or adjusted under 35 U.S.C. 154(b) by 734 days.

This patent is subject to a terminal disclaimer.

(21) Appl. No.: 10/656,592

(22) Filed: Sep. 4, 2003

(65) Prior Publication Data

US 2004/0059200 A1   Mar. 25, 2004

Related U.S. Application Data

(60) Division of application No. 09/924,216, filed on Aug. 7, 2001, now Pat. No. 6,641,532, which is a continuation of application No. 09/326,971, filed on Jun. 7, 1999, now Pat. No. 6,270,456, which is a continuation of application No. 08/893,402, filed on Jul. 11, 1997, now Pat. No. 5,935,060.

(60) Provisional application No. 60/021,615, filed on Jul. 12, 1996, provisional application No. 60/021,614, filed on Jul. 12, 1996.

(51) Int. Cl.
*A61B 5/00* (2006.01)

(52) U.S. Cl. .................................................. 600/300

(58) Field of Classification Search ..................... None
See application file for complete search history.

(56) References Cited

U.S. PATENT DOCUMENTS 4,220,160 A   9/1980   Kimball et al.

(Continued)

FOREIGN PATENT DOCUMENTS

DE    44 30 164 A    2/1996

(Continued)

OTHER PUBLICATIONS

The Alpha Media Catalog, *Advertisement*, Oct. 1993, "Physician's Database Manager" and "Iliad."

(Continued)

*Primary Examiner*—Robert L. Nasser
(74) *Attorney, Agent, or Firm*—Knobbe Martens Olson & Bear LLP

(57) ABSTRACT

A system and method for providing computerized, knowledge-based medical diagnostic advice. The medical advice is provided to the general public over a network, such as a telephone network with the use of a telephone or the Internet with the use of an Internet access device. Alternatively, the medical advice can be provided to a patient in a stand-alone mode by use of a computer. The invention utilizes a list-based processing method of generating and executing diagnostic scripts. For the purpose of diagnosing a health problem of a patient, medical knowledge is organized into a list of the diseases to be considered. Each disease on the disease list includes a list of symptoms that is checked in a patient. Each symptom on the symptom list is then further described as a response to a list of one or more questions asked of the patient about the symptom. This triply-nested list structure is converted by suitable data structure transformations into a script that is stored. When a patient requires diagnosis, the script is played back as a sequence of questions. The responses of the patient are analyzed and converted into symptoms. The symptoms are accumulated into diseases. Finally the diseases are selected and reported as a diagnosis.

44 Claims, 20 Drawing Sheets

U.S. PATENT DOCUMENTS

| | | | |
|---|---|---|---|
| 4,290,114 A | 9/1981 | Sinay | |
| 4,315,309 A | 2/1982 | Coli | |
| 4,337,377 A | 6/1982 | Van Riper et al. | |
| 4,428,381 A | 1/1984 | Hepp | |
| 4,458,693 A | 7/1984 | Badzinski et al. | |
| 4,465,077 A | 8/1984 | Schneider | |
| 4,531,527 A | 7/1985 | Reinhold, Jr. et al. | |
| 4,606,352 A | 8/1986 | Geddes et al. | |
| 4,712,562 A | 12/1987 | Ohayon et al. | |
| 4,733,354 A | 3/1988 | Potter et al. | |
| 4,825,869 A | 5/1989 | Sasmor et al. | |
| 4,838,275 A | 6/1989 | Lee | |
| 4,839,822 A | 6/1989 | Dormond et al. | |
| 4,868,763 A | 9/1989 | Masui et al. | |
| 4,945,476 A | 7/1990 | Bodick et al. | |
| 4,962,491 A | 10/1990 | Schaeffer | |
| 4,974,607 A | 12/1990 | Miwa | |
| 4,975,840 A | 12/1990 | DeTore et al. | |
| 5,012,411 A | 4/1991 | Policastro et al. | |
| 5,023,785 A | 6/1991 | Adrion et al. | |
| 5,030,948 A | 7/1991 | Rush | |
| 5,054,493 A | 10/1991 | Cohn et al. | |
| 5,099,424 A | 3/1992 | Schneiderman | |
| 5,113,869 A | 5/1992 | Nappholz et al. | |
| 5,193,541 A | 3/1993 | Hatsuwi | |
| 5,235,510 A | 8/1993 | Yamada et al. | |
| 5,255,187 A | 10/1993 | Sorensen | |
| 5,299,121 A | 3/1994 | Brill et al. | |
| 5,357,427 A | 10/1994 | Langen et al. | |
| 5,390,238 A | 2/1995 | Kirk et al. | |
| 5,404,292 A | 4/1995 | Hendrickson | |
| 5,415,167 A | 5/1995 | Wilk | |
| 5,421,343 A | 6/1995 | Feng | |
| 5,435,324 A | 7/1995 | Brill | |
| 5,437,278 A | 8/1995 | Wilk | |
| 5,471,382 A | 11/1995 | Tallman et al. | |
| 5,486,999 A | 1/1996 | Mebane | |
| 5,517,405 A | 5/1996 | McAndrew et al. | |
| 5,553,609 A | 9/1996 | Chen et al. | |
| 5,572,421 A | 11/1996 | Altman et al. | |
| 5,583,758 A | 12/1996 | McIlroy et al. | |
| 5,619,991 A | 4/1997 | Sloane | |
| 5,633,910 A | 5/1997 | Cohen | |
| 5,642,936 A * | 7/1997 | Evans | 600/300 |
| 5,722,418 A | 3/1998 | Bro | |
| 5,746,204 A | 5/1998 | Schauss | |
| 5,794,208 A | 8/1998 | Goltra | |
| 5,800,347 A | 9/1998 | Skates et al. | |
| 5,802,495 A | 9/1998 | Goltra | |
| 5,812,984 A | 9/1998 | Goltra | |
| 5,823,949 A | 10/1998 | Goltra | |
| 5,953,704 A | 9/1999 | McIlroy et al. | |
| 6,001,060 A | 12/1999 | Churchill et al. | |
| 6,032,678 A | 3/2000 | Rottem | |
| 6,081,786 A | 6/2000 | Barry et al. | |
| 6,106,459 A | 8/2000 | Clawson | |
| 6,177,940 B1 | 1/2001 | Bond et al. | |
| 6,248,063 B1 | 6/2001 | Barnhill et al. | |
| 6,270,456 B1 | 8/2001 | Iliff | |
| 6,601,055 B1 | 7/2003 | Roberts | |
| 6,900,807 B1 | 5/2005 | Liongosari et al. | |
| 2002/0029157 A1 | 3/2002 | Marchosky | |
| 2002/0186818 A1 | 12/2002 | Arnaud et al. | |
| 2003/0181790 A1 | 9/2003 | David et al. | |
| 2005/0234306 A1 | 10/2005 | Schulte et al. | |

FOREIGN PATENT DOCUMENTS

| | | |
|---|---|---|
| EP | 0 320 749 A2 | 12/1988 |
| EP | 447 710 A1 | 9/1991 |
| EP | 0 531 889 A2 | 3/1993 |
| EP | 0 531 889 A3 | 3/1993 |
| EP | 0 643 360 A2 | 3/1995 |
| EP | 0 720 336 A2 | 7/1996 |
| EP | 0 720 336 A3 | 7/1996 |
| JP | 08117210 A | 5/1996 |
| JP | 08164127 A | 6/1996 |
| WO | WO 93/23819 | 11/1993 |
| WO | WO 94/00817 | 1/1994 |
| WO | WO 95/06296 | 3/1995 |
| WO | WO 95/19604 | 7/1995 |

OTHER PUBLICATIONS

Arthur D. Little, Inc., Acorn Park, Cambridge, MA, Jul. 1992, "Can Telecommunications Help Solve America's Health Care Problems?".

Becher, Ernst, *NTZ*, 33:304, 1980, "Femmeldewesen fur soziale Dienste in Entwicklungsländem."

Bergman, Rhonda, *Journal of the American Hospital Association*, 67(10:52, May 20, 1993, "Computers make 'house calls' to patients; Harvard Community Health Plan offers computerized information service to patients."

Bowden, K.F., et al., *Information Processing*, 71:1398-1406, 1972, "Data structures for general practice records."

Cimino, James J., et al., *IEEE/Ninth Annual Conference of the Engineering in Medicine and Biology Society*, 1987, "Dxplain: An interactive knowledge base for assistance in medical diagnostic decisions."

Conrath, David W., et al., *IEEE Transactions on Communications*, COM-23(10):1119-1126, 1975, "A preliminary evaluation of alternative telecommunication systems for the delivery of primary health care to remote areas."

Currid, Cheryl, *PC Week*, Sep. 17, 1990, "Risky Business: doctors, lawyers shy away from computer technology."

Doheny, Kathleen, *LA Times Magazine*, p. 8, Aug. 4, 1991, "Hack attack."

Frenger, Paul, *IEEE Frontiers of Computers in Medicine*, 1982, "Details of a database management system for a telephone medical consultation service."

Frenger, Paul, *ISA*, pp. 103-107, 1983, "Advanced techniques used to create a telephone medical consultation service."

Frudenheim, Milt, *The New York Times, Business and Health*, p. D2, Jun. 25, 1991, "Computer says take 2 aspirin."

Gini, G. and Gini M., *International Journal of Bio-Medical Computing*, 11:99-113, 1980, "A serial model for computer assisted medical diagnosis."

Goldbard, Gary A., *Class Notes*, Tulane Medicine, Tulane University Medical Center, 1430 Tulane Ave., New Orleans, LA 70112-2699, p. 26, Jun. 1991.

Gome, Amanda, *Herald-Sun*, p. 13, Nov. 19, 1991, "A picture of success."

Fisher et al., "Great Expectations: Expectation-based reasoning in Medical Diagnosis," Proceedings of the 12th Annual Symposium on Computer Applications in Medical Care, Nov. 6, 1988, pp. 38-42.

Larsson et al., "An Expert System Interface for an Identification Program," Automatica, Pergamon Press Ltd., Oxford, GB., vol. 27, No. 6, Nov. 1, 1991.

Gini et al., "A Serial Model for Computer Assisted Medical Diagnosis," Int. J. Bio-Medical Computing (11) (1980) pp. 99-113.

Gale et al., *Medical Diagnosis From Student to Clinician*, p. 1-22 (1983).

Office Action for Japanese Patent Application No. 506146/98 (and English language translation).

Gorry, G. Anthony, *Bulletin of the Operations Research Society of America*, 19(2), 1971, "FA6.3 Automating Judgmental decision making in medicine."

Hudson, et al., *IEEE Computer Society Press*, vol. 2., pp. 429-435, 1989, "Human-Computer Interaction in a Medical Decision Support System."

Kerr, Jennifer, *San Diego Union-Tribune*, p. A3, Sunday, Jul. 18, 1993, "Phone is link to health-care Information."

Laughlin, Michael L., ed., *Computers in Health Care*, pp. 32-37, Nov. 1992, "Telecommunications may offer poor a 'road' to healthcare."

Levin, Carol, *PC Magazine*, p. 32, Mar. 16, 1993, "Patient, heal thyself."

Mallory, Jim, Newsbytes, American Association for the Advancement of Science, *Panel Discussion*, Feb. 19, 1992, "Computers now giving medical advice."

McDonald, Michael D. and Blum, Henrik L., Environmental Science and Policy Institute, 1992, "Health in the information Age: The Emergence of Health Oriented telecommunication Applications."

*New York Times*, p. 18, Jul. 13, 1991, "System helps doctors keep up to date."

O'Neil, et al., *Conference Paper*, IEEE Coll. On Computer Based Diagnosis, p. 8/1-4, 1989, "Diagnostic Support in the Oxford System of Medicine."

Rose, J., ed., Proceedings of the First International Congress of Cybernetics, London, Gordon and breach Science Publishers, pp. 803-811, 1969, "Progress of cybernetics, vol. 2 cybernetics and industry, social and economic consequences, cybernetics and artifacts."

Rymon, et al., *IEEE Transactions on Systems, Man, and Cybernetics*, 23(6): 1551-1560, Nov./Dec. 1993, "Progressive Horizon Planning-Planning Exploratory-Corrective Behavior."

Sacks, Terry, *San Diego Union-Tribune*, p. E-16, Mar. 24, 1992, "Pocket computer may cure technology-shy physicians."

Salvans, P. Ferrer, and Alonso L. Vallès, Computer Biol. Med., 20(6): 433-443, 1990, "An epidemiologic approach to computerized medical diagnosis-AEDMI program."

San Diego Emergency Physicians Society, *Meeting Minutes*, Regular Oct. 1991 Meeting, P.O. Box 16685, San Diego, CA 92176 first page.

Schild, W., et al., IBM J. Res. Develop., 22(5):518-532, 1978, "Computer-aided diagnosis with an application to endocrinology."

Shapiro, *Encyclopedia of Artificial Intelligence*, 2nd Edition, vol. 2, pp. 916-926, John Wiley & sons, Inc., 1992.

Shortliffe, Edward H., Expert Systems and Al Applications, pp. 323-333, 1980, "Consultation system for physicians: the role of artificial intelligence techniques."

Sloane, L., *New York Times*, p. 16, Jul. 13, 1991, "For round-the clock diagnosis, just pick up your telephone."

Smothers, R., *New York Times*, Sep. 16, 1992, "New video technology lets doctors examine patients many miles away."

Technical Computing, 6(9), Aug. 1991, "Harvard Community Health Plan testing computerized service that answers health-care questions."

Thorpe, C. William, et al., *Computer Methods and Programs in Biomedicine, Section II, Systems and programs*, 36:33-43, 1991, "A microcomputer-based interactive cough sound analysis system."

Wagner, J., et al., *Conference Paper of expert Systems and Decision Support in Medicine*, 33rd Annual Meeting of the GMDS EFMI Special Topic Meeting, "A knowledge-based system for interactive medical diagnosis encoding," 1988.

Waltz, Nancy, The Associated Press, *Business News*, Jun. 25, 1991, "Computer system aims to wipe out medical paperwork."

Waterman, *A Guide to Expert Systems*, Addison-Wesley Publishing Co., pp. 46-47 and 272-288, 1986.

Weinstock, Edward, *Cover*, Avant-Garde, 1984, "An Apple a Day™."

Werner, et al., *Conference Paper*, IEEE Engineering in Medicine and Biology, 3 pages, 1989, "interlocutor: Conferring with an Expert Diagnostic Consultant . . . ."

"Encyclopedia of Computer Science and Technology", J. Belzer, et al., Marcel Dekker, Inc., NY (US), 1978, pp. 78-79 and 114-115.

Hile, et al., "Reliability of an Automated Decision Support System for Behavioral Treatment Planning: Preliminary Results from the Mental Retardation-Expert," Computers in Human Services, vol. 10(4) 1994, pp. 19-29.

Proc. Of the 13th Annual Northeast Bioengineering Conference, 12-13.3. 1987, C.W. Starr et al.: "A microcomputer-based medical expert system shell using a weight-threshold decision mechanism," pp. 279-281.

Der Denkprozeβ—Vom Symptom Zur Diagnose (with English language translation), 1980.

"Anamnese Und Befund" by J. Dahmer (Georg Thieme Verlag 1981), pp. 22-25, 44-47, 292-295 and 371-375 (with English language translation of p. 22-24, 44-45, 292, 295).

Starr et al., "Gycon: A Microcomputer Based Gynecological Consultant," *Proceedings of International Computer Symposium*, pp. 1678-1684 (1986).

* cited by examiner

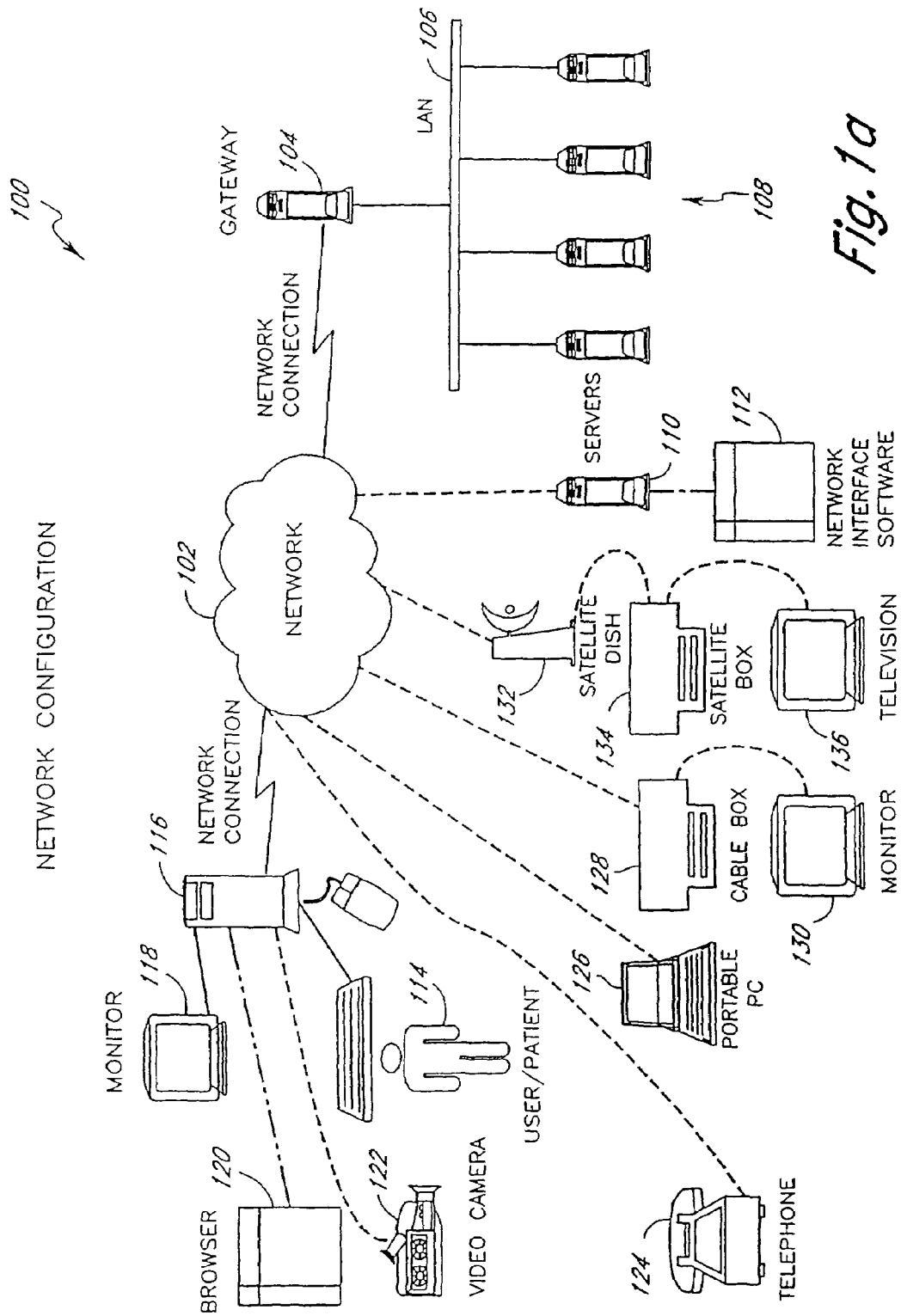

COMPUTERIZED MEDICAL DIAGNOSTIC SYSTEM UTILIZING LIST-BASED PROCESSING

RELATED APPLICATIONS

This application is a divisional of U.S. patent application Ser. No. 09/924,216, filed Aug. 7, 2001, now U.S. Pat. No. 6,641,532 which is a continuation of U.S. patent application Ser. No. 09/326,971, filed Jun. 7, 1999, now U.S. Pat. No. 6,270,456, which is a continuation of U.S. patent application Ser. No. 08/893,402, filed Jul. 11, 1997, now U.S. Pat. No. 5,935,060 and takes priority under §119(e) from U.S. provisional applications 60/021,614 and 60/021,615, filed Jul. 12, 1996, both of which are now abandoned. U.S. patent application Ser. No. 08/893,402, filed Jul. 11, 1997, now U.S. Pat. No. 5,935,060 is a continuation in part of U.S. patent application Ser. No. 08/176,041, now U.S. Pat. No. 5,660,176 and is related to U.S. patent application Ser. No. 08/176,857, now U.S. Pat. No. 5,724,968, and U.S. patent application Ser. No. 08/176,858, now U.S. Pat. No. 5,594,638, all of which were filed on Dec. 29, 1993.

BACKGROUND

1. Field of the Invention

Aspects of the present invention relate to computerized medical diagnostic systems. More specifically, embodiments of the present invention relate to a computerized system for time-based diagnosis of a patient's complaint by use of dynamic data structures.

2. Description of the Related Technology

Health care costs currently represent a significant portion of the United States Gross National Product and are rising faster than any other component of the Consumer Price Index. Moreover, usually because of an inability to pay for medical services, many people are deprived of access to even the most basic medical care and information.

Many people delay in obtaining, or are prevented from seeking, medical attention because of cost, time constraints, or inconvenience. If the public had universal, unrestricted, and easy access to medical information, many diseases could be prevented. Likewise, the early detection and treatment of numerous diseases could keep many patients from reaching the advanced stages of illness, the treatment of which is a significant part of the financial burden attributed to our nation's health care system. It is obvious that the United States is facing health-related issues of enormous proportions and that present solutions are not robust.

Previous attempts at tackling the health care problem have involved various forms of automation. Some of these attempts have been in the form of a dial-in library of answers to medical questions. Other attempts have targeted providing doctors with computerized aids for use during a patient examination. These methods involve static procedures or algorithms. What is desired is an automated way of providing to a patient medical advice and diagnosis that is quick, efficient and accurate. Such a medical advice system should be modular to allow expansion for new types of medical problems or methods of detection.

One way of conducting an interview of a patient includes medical diagnostic scripts. What is needed is an efficient method of representing the medical knowledge of experts in their specialties in a script format. The scripts should utilize dynamic structures to quickly and efficiently reach a diagnosis of the patient.

SUMMARY OF THE INVENTION

List-Based Processing is a method of diagnosing diseases that works by arranging diseases, symptoms, and questions into a set of nested Disease, Symptom, and Question (DSQ) lists in such a way that the lists can be processed to generate a dialogue with a patient. Each question to the patient generates one of a set of defined responses, and each response generates one of a set of defined questions. This establishes a dialogue that elicits symptoms from the patient. The symptoms are processed and weighted to rule diseases in or out. The set of ruled-in diseases establishes the diagnosis. A List-Based Processing system organizes medical knowledge into formal, structured lists or arrays, and then applies a special algorithm to those lists to automatically select the next question. The responses to the questions lead to more questions and ultimately to a diagnosis.

In one embodiment of the invention, there is a computerized medical diagnostic system, comprising a list of diseases, each disease associated with a list of symptoms, and each symptom associated with a list of questions; and a script engine operating on a computer and configured to repetitively ask questions to elicit responses, the responses establishing symptoms, each established symptom contributing a weight to an accumulated total weight for a disease, and determine whether the accumulated total weight for a disease reaches or passes a threshold so as to declare a diagnosis.

In another embodiment of the invention, there is a computerized medical diagnostic method, comprising providing a list of diseases, each disease associated with a list of symptoms, and each symptom associated with a list of questions; and executing a script engine on a computer comprising repetitively asking questions to elicit responses; establishing symptoms based on the responses; contributing a weight to an accumulated total weight for a disease based on each established symptom; and determining whether the accumulated total weight for a disease reaches or passes a threshold so as to declare a diagnosis.

In another embodiment of the invention, there is a computer usable medium having computer readable program code embodied therein for performing a computerized process used in medical diagnosis, the computer readable code comprising instructions for providing a list of diseases, each disease associated with a list of symptoms, and each symptom associated with a list of questions; and executing a script engine comprising repetitively asking questions to elicit responses from a patient; establishing symptoms based on the responses; contributing a weight to an accumulated total weight for a disease based on each established symptom; and determining whether the accumulated total weight for a disease reaches or passes a threshold so as to declare a diagnosis.

In yet another embodiment of the invention, there is a computerized medical diagnostic system, comprising a list of diseases, each disease associated with a list of symptoms, and each symptom associated with a list of questions; and a script engine operating on a computer and configured to repetitively ask questions to elicit responses from a patient, the responses establishing symptoms, each established symptom contributing a weight to an accumulated total weight for a disease, and determine whether the accumulated total weight for a disease reaches or passes a threshold so as to declare a diagnosis.

BRIEF DESCRIPTION OF THE DRAWINGS

FIG. 1a is a block diagram illustrating components of a presently preferred embodiment of the computerized medical diagnostic and treatment advice (MDATA) system of the present invention;

FIG. 1b is a block diagram illustrating components of the user/patient computer of the MDATA system shown on FIG. 1a;

FIG. 2 is a block diagram illustrating a set of processes, files, and databases utilized by the system of FIG. 1a;

FIG. 4a is a flow diagram of an assign diseases portion of the "collect and organize medical knowledge" process shown in FIG. 3a;

FIG. 4b is a flow diagram of a capture disease knowledge portion of the "collect and organize medical knowledge process" shown in FIG. 3a;

FIG. 5 is a flow diagram of the "script compiler" process shown in FIG. 3a;

FIG. 8b is a flow diagram of the "distribute advice" process shown in FIG. 8a;

FIG. 10 is a block diagram showing a portion of the lists utilized during operation of the DSQ list script engine shown in FIG. 8a;

FIG. 11 is another flow diagram of the "DSQ list script engine" process shown in FIG. 8a;

FIG. 15 is a high-level flow diagram of an alternative embodiment for generating medical advice or a diagnosis in the MDATA system of FIG. 1a.

DETAILED DESCRIPTION

Figure 1B:
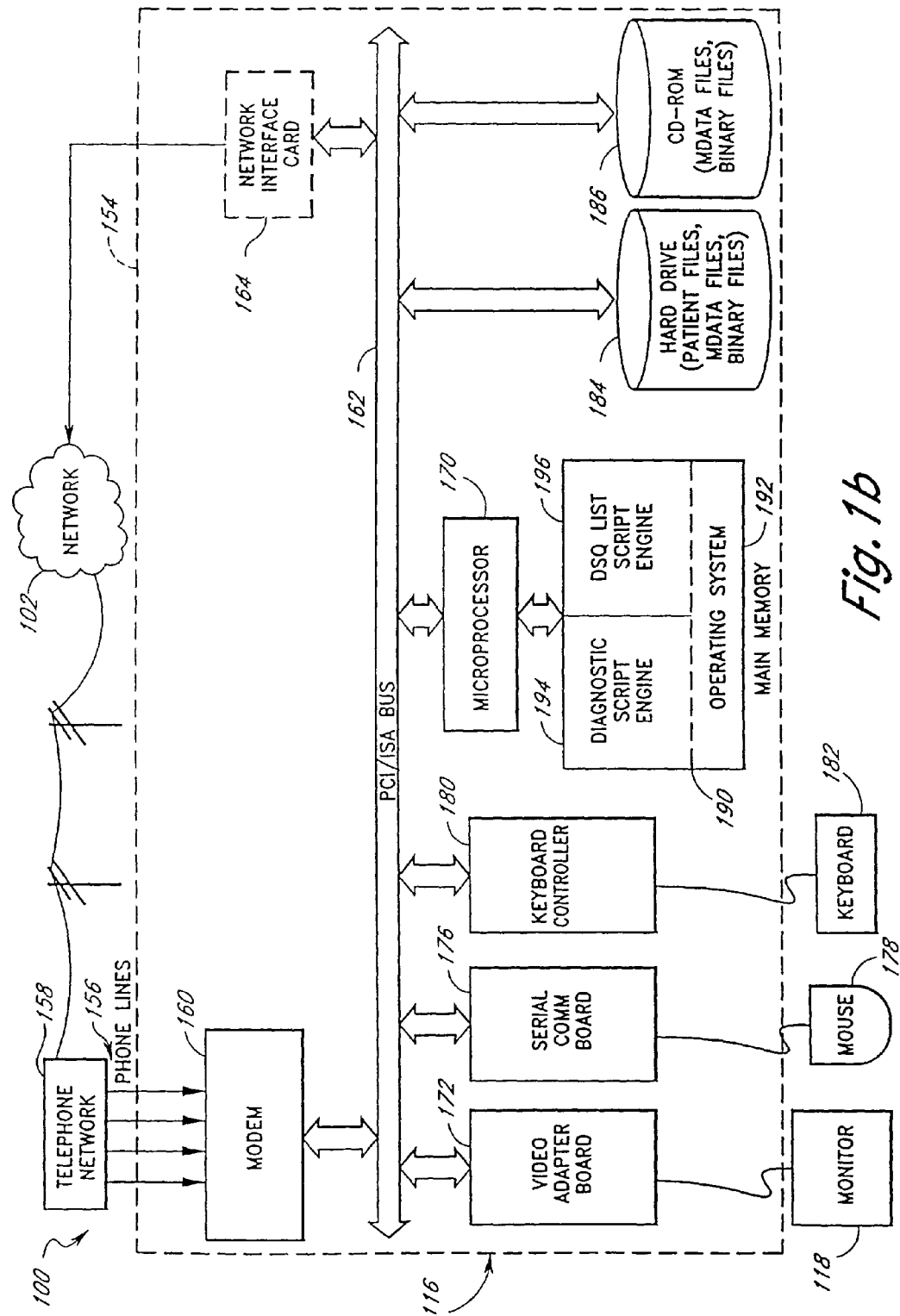

The following detailed description presents a description of certain specific embodiments of the present invention. However, the present invention may be embodied in a multitude of different ways as defined and covered by the claims. In this description, reference is made to the drawings wherein like parts are designated with like numerals throughout.

For convenience, the discussion of the preferred embodiment will be organized into the following principal sections: System Overview, Medical Diagnostic Scripts, Knowledge Capture Details, Script Generation Details, Script Execution Details, and Advantages of List-Based Processing.

I. System Overview

A Medical Diagnostic and Treatment Advice (MDATA) system is a computer system that conducts automated interviews of patients for the purpose of establishing a medical diagnosis. To conduct the interviews, MDATA uses a database of Medical Diagnostic Scripts (MDS). Each MDS contains the data and commands needed to interview a patient for a specific medical condition and to output a diagnosis. Scripts are supported by other MDATA databases of diseases, symptoms, treatments, medications, specialists—in short, all information required for medical diagnosis and advice. Symptoms can be defined as a piece of historical information, a piece of information elicited from a physical examination, e.g., physical signs usually from a self-examination, the results of a laboratory test, or the results of an imaging modality of choice.

Referring to FIG. 1a, a block diagram of a presently preferred embodiment of the MDATA system 100 will be described. The MDATA system 100 includes a network "cloud" 102, which may represent a local area network (LAN), a wide area network (WAN), the Internet, or another connection service.

The MDATA programs and databases preferably reside on a group of servers 108 that are preferably interconnected by a LAN 106 and a gateway 104 to the network 102. Alternatively, the MDATA programs and databases reside on a single server 110 that utilizes network interface hardware and software 112. The MDATA servers 108/110 store the disease/symptom/question (DSQ) lists described hereinbelow.

The network 102 may connect to a user computer 116, for example, by use of a modem or by use of a network interface card. A user 114 at computer 116 may utilize a browser 120 to remotely access the MDATA programs using a keyboard and/or pointing device and a visual display, such as monitor 118. Alternatively, the browser 120 is not utilized when the MDATA programs are executed in a local mode on computer 116. A video camera 122 may be optionally connected to the computer 116 to provide visual input, such as visual symptoms.

Various other devices may be used to communicate with the MDATA servers 108/110. If the servers are equipped with voice recognition or DTMF hardware, the user can communicate with the MDATA program by use of a telephone 124. A telephonic embodiment is described in Applicant's application entitled "Computerized Medical Diagnostic and Treatment Advice System," U.S. Ser. No. 08/176,041, now U.S. Pat. No. 5,660,176, which is hereby incorporated by reference. Other connection devices for communicating with the MDATA servers 108/110 include a portable personal computer with a modem or wireless connection interface, a cable interface device 128 connected to a visual display 130, or a satellite dish 132 connected to a satellite receiver 134 and a television 136. Other ways of allowing communication between the user 114 and the MDATA servers 108/110 are envisioned.

Referring to FIG. 1b, a diagram of a presently preferred user/patient computer shows several possible interconnections to the network. To "play" a script, a special program called a Script Engine is used, which reads a MDS file and uses its codes to perform interview actions, such as outputting a question to a patient and inputting an answer. The scripts also collect the answers from the patient, evaluate the answers, issue a diagnosis, and update the patient's medical record. The script engine preferably resides in the user computer. The script engine may be stored on the hard drive or CD-ROM, and is loaded into the main memory or a cache for execution.

The components of a presently preferred computer 116, utilized by a user 114 of the computerized MDATA system 100 of the present invention, are shown in FIG. 1b. Alternatively, other devices for conducting a medical interview, such as those shown in FIG. 1a, can be utilized in place of the computer 116.

The computer 102 includes a plurality of components within an enclosure 116. A telephone line 106 interfaces the public telephone network 158 to the computer 116 via a modem 160. The telephone network 158 may connect to the network 102, which has connections with the MDATA system server(s) 108/110. Alternatively, the user may connect to the network 102 by use of a network interface card 164.

Throughout this document, the words user and patient are used interchangeably. However, it will be understood that the user may be acting as a proxy for the patient. If this is the case, the user is registered as an assistant for the patient.

The hardware and system software are assembled with two basic concepts in mind: portability to other operating systems and the use of industry standard components. In this way, the system can be more flexible and will allow free market competition to continually improve the product, while, at the same time, decreasing costs. While specific hardware and software may be referenced, it will be understood that a panoply of different components could be used in the present system.

The computer 116 preferably is a personal computer with an Intel Pentium microprocessor 170. Other computers, such as an Apple Macintosh, an Amiga, a Digital Equipment Corporation VAX, or an IBM mainframe, could also be utilized. The modem 160 or the network interface card 164 connect to an industry standard architecture (ISA) or a peripheral component interconnect (PCI) bus 162. The bus 162 interconnects the microprocessor 170 with a plurality of peripherals through controller circuits (chips or boards).

The computer bus 162 has a plurality of peripherals connected to it through adapters or controllers. A video adapter board 172, preferably at SVGA or better resolution, interconnects to a video monitor 118. A serial communication circuit 176 interfaces with a pointing device, such as a mouse 178. A parallel communication circuit may be used in place of circuit 176 in another embodiment. A keyboard controller circuit 180 interfaces with a keyboard 182. A 500 Mb or greater hard disk drive 184 and an optional CD-ROM drive 186 are preferably attached to the bus 162. The hard disk 184 stores database files such as the patient files, other MDATA files, and binary support files. The CD-ROM drive 186 also stores database files, such as files for the patients using the computer 116, and binary support files.

A main memory 190 connects to the microprocessor 170. In the presently preferred embodiment, the computer 116 preferably operates under the Windows 95 operating system 192. The memory 190 executes a diagnostic script engine 194 and a disease/symptom/question (DSQ) list script engine 196. The script engine software is written in Borland Delphi Pascal, version II.

Figure 2:
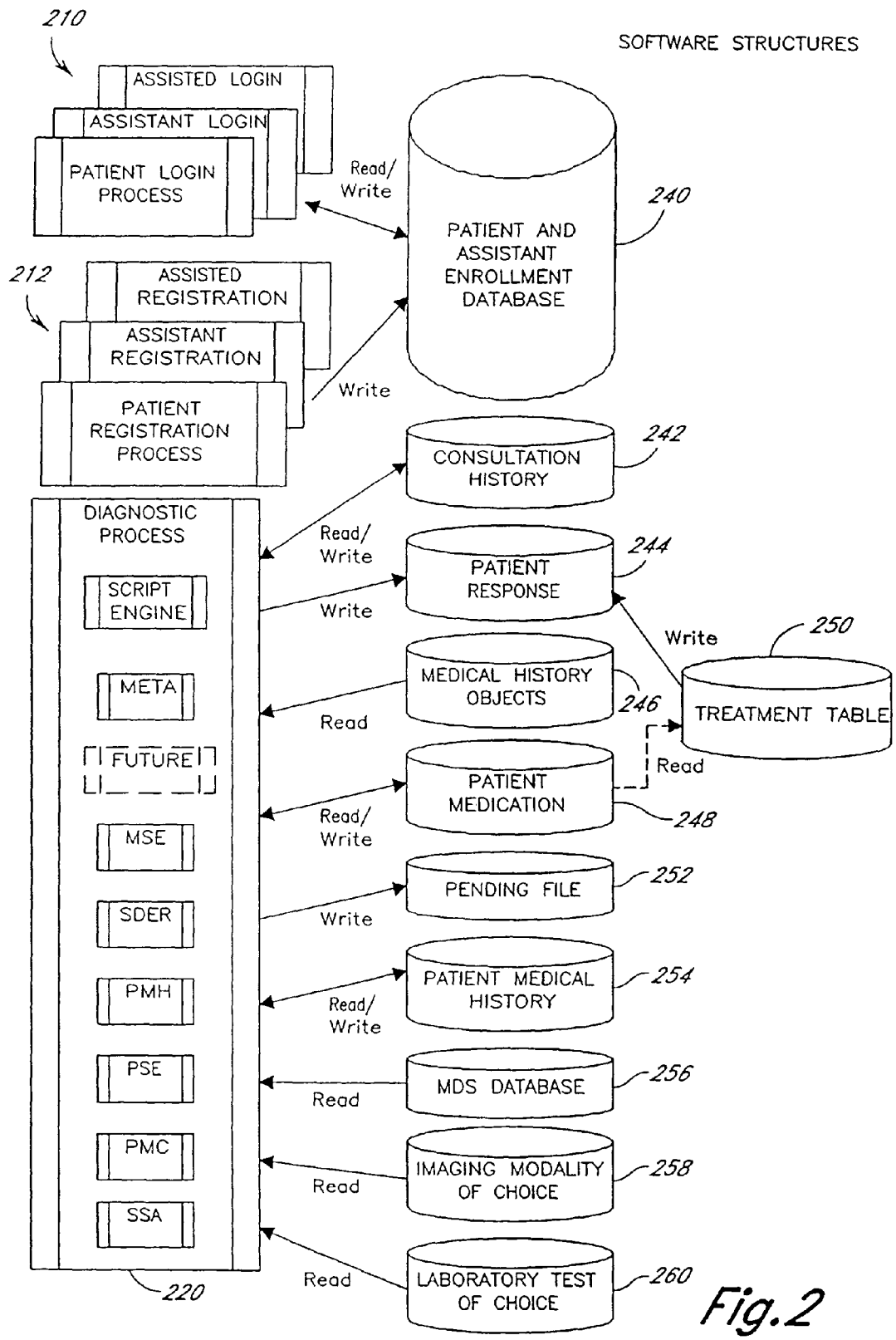

Referring to FIG. 2, a set of processes, files, and databases utilized by the MDATA system 100 will be described. Except for the script engine process, the MDS database, the Imaging Modality database, and the Laboratory Test database, which are described hereinbelow, these processes, files, and databases were described in Applicant's application entitled "Computerized Medical Diagnostic and Treatment Advice System," U.S. Ser. No. 08/176,041, now U.S. Pat. No. 5,660,176.

The MDATA system 100 utilizes several principal processes and related databases. A set of patient login processes 210 is used by the system 100 to identify a patient who has previously registered into the system in one of three ways: 1) by prompting for a patient identification number (PIN); 2) identify an assistant who has previously registered into the system by prompting for an assistant identification number (AIN); 3) identify a patient, having an assistant, who has previously registered into the system by prompting for the patient identification number. A set of processes 212 are used to register a patient or assistant. If the user is the patient, a patient registration process is used by the system to register new or first-time patients. If the user is not the patient, an assistant registration process is used by the system to register new or first-time assistants. Then, if the patient is not already registered, an assisted patient registration process is used by the system to register the patient.

Once a user has logged in or registered, the system provides a choice of processes. The primary process of concern in the current embodiment is the Diagnostic process 220 that performs a patient diagnosis. The evaluation process 220 accesses a laboratory test of choice and imaging modality of choice database to recommend the appropriate tests in this patient at this point in time and a treatment table 250 to obtain current treatment information for a particular disease or diagnosis. In another embodiment, other choices are added to access other medical information processes.

Associated with these processes are a patient and assistant enrollment database 240, a consultation history database 242, a patient response database 244, a medical history objects database 246, a patient medication database 248, a pending database 252, a patient medical history database 254, a medical diagnostic scripts (MDS) database 256, an imaging modality database 258, and a laboratory test database 260.

II. Medical Diagnostic Scripts

A Medical Diagnostic Script (MDS) is a programmed dialogue with a patient for the purpose of generating one or more diagnoses of the patient's condition. Developing an MDS involves several steps such as capturing the medical diagnostic knowledge, expressing it in terms that a patient can understand, arranging it into a useful sequence, compiling it into a playable script, testing it, configuring it for a specific communication medium, embedding it into a collection of other scripts and support databases, and packaging it for use by the patient.

"Writing a script" is considered to mean the early steps of capturing the medical knowledge and processing it into a logical question stream that ultimately leads to a diagnostic conclusion. Obviously, only a physician experienced in diagnosing a specific set of diseases can perform these steps, and the MDATA system has developed several automated methods to support them.

The invention preferably utilizes one particular method, called "list-based processing," which begins with lists of diseases, symptoms, and questions. These lists are then processed into a playable script using a list-based script development tool. Using the script development tool, the author can write and edit the source script, compile it into a playable script file, play the script back, and set various script options to exercise, evaluate, and fine-tune the script.

A list-based script consists of a specially formatted text file in which the author provides the elements of the script in the form of several lists. The top list is a list of diseases which the script will consider. For each disease, the script lists the symptoms and their weights. For each symptom, the author provides a list of questions and their weights that will elicit the symptom. For each question, the author provides multiple text objects, including a preamble text that introduces the question.

After all of the lists have been prepared for a script, the next step is to "compile" the script, i.e. to convert it into a specially encoded script file that can be played back, or "run," for a patient. To run a script in the development phase, the script development tool selects a suitable next disease and a suitable next symptom for that disease. It displays the question text and waits for a reply from the patient. Based on the patient's response, the script development tool updates the disease scores and continues with the next symptom. The script stops when some condition (set by the author) is reached, such as the first disease being ruled in as a diagnosis, or all diseases having been considered.

During the development phase, the script author can set various "options" that will change the way the script selects the next disease and the next symptom, and how long the script will run. This option feature lets the author experiment with the script to find the best settings.

The three main phases of a script, therefore, are: 1) knowledge capture, 2) script generation and 3) script execution. The script author utilizes all three phases in the creation and testing of a script. A patient utilizes the script execution phase during run-time use of the MDATA system 100.

Phases of a Script

1. Knowledge Capture

The knowledge capture phase includes all of the tasks needed to extract from a medical expert the knowledge about diagnosing a given disease and reducing that knowledge to some form useful in generating a script. The phase typically begins with a director of script development expressing a need for a script for diagnosing a disease such as Malaria. It continues with tasks such as defining the scope of the script, researching medical texts, interviewing authors and other experts, formatting the question and response sets, establishing the question sequence, and, if an automated knowledge capturing tool is used, running the question flow in a test setting. This phase ends with a set of source documents, possibly automated, that (at least) contains all of the information needed to write a script that can correctly diagnose the disease, e.g., Malaria/Not Malaria when it is fed test responses for a patient that does/not have Malaria. Nothing is known at this point about the ultimate form of the script, the platform on which it will run, or even the natural language it will be using to communicate with the patient.

2. Script Generation

In the script generation phase, the script is generated as a relatively small diagnostic algorithm captured in software. In this phase, the goal is to let the script be an automated representation of the author's approach to diagnosing a disease or other medical problem, such as Malaria. The script contains data and processes to produce a good first question, to weigh the response, to use the response to generate another question, and so on until the script can finally tell its caller that the responses indicate Malaria or Not Malaria, and the associated level of confidence.

Note that a script is not a stand alone program that can be run for a real patient. The script preferably only knows about a single chief complaint, such as Malaria, and does not diagnose other medical problems such as Gout or Asthma.

This script is destined to become one of approximately 40,000 scripts in the Script Database, in much different form and format. The script now has to be translated into the appropriate human language (German, Spanish), supplemented with appropriate error handling mechanisms, generated into the appropriate programming language (C++, Java, HTML), formatted for the appropriate target medium (PC, Mac, Telephone, LAN, WAN, Internet), and linked to the Support System (databases, meta functions, patient records, session logging).

Next, the script undergoes extensive testing in a testbed that feeds the script various canned sets of patient responses, with known acceptable diagnoses, to verify that the script does generate the appropriate output.

Finally, the script is ready to be installed into a production system. It may be stored into a massive Script Database, or packaged into a set of scripts to be written to a CD ROM or shipped via the Internet to a hospital. Whatever the form of the script library used, the script will have to be indexed and registered will be with the Script Manager software. At the end of this phase, the script is at last part of an official, running medical diagnostic system that can be used on real patients for real diagnoses of real problems.

3. Script Execution

In the script execution phase, the script is actually executed, sooner or later. Of course, a session with a patient does not start with a diagnostic script on Malaria. A medical diagnostic system open to the general public obviously has a number of administrative tasks to perform before it gets down to any medical diagnosis. First of all, it does not want a patient acutely deteriorating while we ask for a password and Social Security Number. So the system most likely first runs the Emergency Room (ER) subsystem for anyone who logs on to the MDATA system. The ER subsystem consists of a few dozen scripts that determine whether the patient has any life threatening condition that needs immediate "first aid" therapy or advice. "Is this a medical emergency?", "Does the patient have an airway?", "Is the patient bleeding?" are some of the questions the ER subsystem asks.

After the system weeds out the emergency cases, the system can slow down to identify the patient and determine the Chief Complaint(s). Then the system invokes the Script Routing subsystem, whose job is to determine the patient's general problem area. Based on this information, the Script Routing system next selects a sequence of top-level scripts that are appropriate to the patient's Chief Complaint. For example, for fever, after the more obvious scripts for Appendicitis, Intestinal Flu, Food Poisoning have indicated "No Diagnosis," the Routing script may finally decide to try Malaria. Now, at last, the sample Malaria script we have developed in this document is played.

Scripts are not programs that run themselves. Scripts are data streams that are run by a "script engine" that searches the script for the next question to ask of the patient, and formats the question for transmission (to a screen, a telephone line, or an Internet site). The patient responses are also captured by the script engine, formatted for the script, and used to select the next question from the script. This interplay of the script and its script engine may consider the patient's medical record, the information provided so far during this session, and even some meta functions to determine the next question. At the end of the script, the process returns control to the Tropical Disease Routing Script and says, in effect, "this patient's responses indicate Malaria Falciparum with a weight of 1350 out of 1000," or "this patient's responses only add up to 420 out of 1000, so I rule out Malaria." The Routing script that called the Malaria script in the first place may now decide to access another diagnostic script, or may decide to return to its caller some response such as "the patient's responses indicate only a 275/1000 likelihood of having any tropical disease."

Script Features

Time-Based Diagnostic Scripts

The Time-Based Diagnostic Script concept extends the DSQ diagnostic scripts in the time dimension. Instead of just one diagnostic script, the script author now submits several scripts, e.g., one for each hour into the disease process. Scripts are generated at an elapsed time from the beginning of symptoms, according to the best judgment of the author. For example, a myocardial infarction script would use one hour or less as an interval, while malaria would not. At run time, the diagnostic system uses the diagnostic script closest to the patient's case. The script has implied symptoms that add extra weight to diseases that match the predicted pattern.

The system asks the patient when the symptoms started, and, partially based on that information, selects the appropriate script from the time-based set of scripts. Once the right script is selected, the script is executed. That is, each script of a set of time-based scripts may have somewhat different symptoms and weights, so that the author sets up time-based symptoms with extra weights for those diseases whose time-pattern matches the patient's. These weights are automatically added by the script engine as it runs. Note that these time-based symptoms will be Implied Symptoms, described hereinbelow.

Each algorithm author must compose, assign, or calculate the questions and the appropriate values at (for instance) each hour as the disease progresses. Then, when the patient consults the system, one of the first questions to ask is "When (or how long ago) did your symptoms begin?" Then that patient will interact with the script that is closest to the lapsed time since the symptoms(s) began.

Implied Symptoms

Note that a "symptom" is defined as any data item known about a patient, directly or indirectly, including name, age, gender, and so forth. An Implied Symptom is a symptom that is established based on the presence or absence of one or more other symptoms The Implied Symptom concepts allows the script author to tell the script engine that any given symptom (or set of symptoms) implies or denies one or more other symptoms. This lets the author embody real-world relationships into the List-Based script, which, in turn, lets the LB Engine make logical inferences that eliminate superfluous questions from the list and make the script more focused.

As an obvious example, a patient who is a man does not have to be asked questions related to the female reproductive system. A human doctor knows this implicitly, but the script engine needs to be told. The script author simply makes a list of symptoms in the form:

IF Symptom A THEN Symptom B.

For example:

"patient is male" implies "patient is NOT female," and

"patient had Appendectomy" implies "patient has no Appendix."

Using the logical operators such as AND, OR or NOT, it is possible to build quite complicated symptom relationships that are triggered by relatively few questions.

Implied Symptoms are listed in the source script as a table of "IF A THEN B" type statements. Whenever the engine receives a new symptom from the patient, it also checks the Implied Symptom table to see if any other symptoms are implied.

Synergistic Symptoms

Synergistic Symptoms are symptoms that indicate that, in any given patient, a certain set of other symptoms is present that have special diagnostic significance when they occur together. In a DSQ List-Based source script, each symptom has a certain specific weight toward diagnosing a disease, but the presence of a certain set may lend extra weight toward a diagnosis. For example, Malaria is classically diagnosed starting with the presence of Chills, Fever, and Sweating (which are caused as the Malaria-causing agent goes through its reproductive cycle in the blood). The presence of Chills or Fever or Sweating separately would probably not necessarily suggest pursuing Malaria as a diagnosis in a patient, but the assertion of all three of these symptoms should trigger an inquiry about Malaria. The concept of Synergistic Symptoms supports this internal trigger with a statement such as:

"has Chills" AND "has Fever" AND "has Sweating" implies "Possible Malaria." Synergistic Symptoms also have an important use in defining a Syndrome, i.e., particular collections of symptoms that occur together so often that, to the lay public, they have their own name, such as AIDS. The script author can use Synergistic Symptoms to define a Syndrome that is important to him/her.

III. Knowledge Capture Details

The initial task of knowledge capture for a script is identifying the diseases to be included in the script, assigning a priority to each disease, and assigning medical specialists to develop the portions of the script for their assigned diseases. Each medical specialist then generates the appropriate lists needed for the diseases. This can be summarized as follows:

define the scope of diseases to be covered;

list the diseases and their symptoms;

assign rankings, priorities, and weights to diseases and symptoms;

design properly worded and weighted questions that will elicit the symptoms;

format the disease, symptom, and question lists;

pre-test the lists, using test tools specially developed for the purpose; and write the lists as text files, using any ASCII-capable word processor.

The list-based processing method begins with a set of coordinated lists that captures the elements of diagnosing a particular health problem. In this phase, medical experts record their diagnostic skills and techniques in the form of several lists. To do this, the experts preferably can use any commercially available word processor software that is capable of generating an ASCII output file.

The ASCII lists for a script consist of three types of lists that are nested as follows:

one Disease List that identifies all the diseases the script will consider, and ranks them in the order they should be considered for diagnosis;

one Symptom List for each disease that identifies the symptoms and assigns a weight to each symptom to define the contribution it makes to diagnosing the disease;

one Question List for each symptom that identifies one or more weighted questions that will elicit the symptom from a patient.

For the purpose of automated medical diagnoses, medical diagnosis data is organized into a hierarchical classification that is based on the general concept that diseases have symptoms, and symptoms are elicited from the patient by questions.

A "disease" is a health condition that requires treatment or attention such as illness, ailment, affliction, condition, state, problem, obstruction, malfunction, and so forth. To diagnose a patient with a given complaint, the MDATA system begins with a list of possible diseases that exhibit the complaint and reduces this to a list of diagnoses, based on the patient's answers.

A "symptom" is any information that the MDATA system has about the patient. This includes:

patient identification (e.g., name, address, HMO, age, sex);

patient history (e.g., prior illnesses, parental health information, recent travel to foreign countries);

previous accesses to MDATA (e.g., history of patient complaints and progress);

physical signs (e.g., vital signs) and the results of self- or assisted-physical examination maneuvers;

lab and test results;

signs, manifestations, presentations, aspects, and so forth.

For each disease, a list of symptoms is prepared. Each symptom is assigned a weight, which represents a likelihood that the patient has the disease, given the symptom. To simplify calculations, the MDATA system uses a ruled-in threshold value of 1,000 to declare a disease as diagnosed, although other thresholds may be used. The system also utilizes a ruled-out threshold to officially declare that the patient does not have the disease. Both the ruled-in threshold and the ruled-out threshold may be modified by a sensitivity factor set. This permits customized threshold levels, for example, for individual patients. The sensitivity factor set will be further discussed hereinbelow.

In practice, the weight is a measure of the diagnosing physician's willingness to rule the disease in, given the symptom. The weight can also be used as a Conditional Probability that the patient has the disease, given the symptom. This can be used, if convenient, to apply a Bayesian Probability analysis to the symptoms.

A symptom is elicited by a set of one or more questions, often interlaced with information and instructions on how to answer the question. The set of nodes needed to elicit a symptom is called a "flow" because it typically involves a branching flow of questions, often drawn on a small flowchart, that describes how a dialogue with the patient might proceed.

To enter the diagnostic data developed by the medical expert into the MDATA system, the data must be organized and formatted. For this purpose, a text file is used and a text file format was developed. The ASCII character code is preferably utilized, but any well-defined text-character code, such as EBCDIC, could be used.

A script consists of several segments or data groups as follows:

DISEASES to be diagnosed in terms of weighted symptoms;

SYMPTOMS to be elicited by flows or implied by other symptoms;

IMPLICATIONS that logically connect symptoms;

FLOWS consisting of paths through nodes;

PATHS that visit question nodes;

TEXTS that inform and/or advise the patient;

QUESTIONS that ask the patient for a response;

KEYS that signal a specific response from the patient.

These segments are part of the following sections of a script "source" or text file:

Header Section

The Header section contains data that applies to the entire script, such as script format, and the set of symptoms comprising the patient's chief complaint.

Diseases Section

The Diseases section lists the diseases that can be diagnosed by this script, their symptoms, and the symptoms' weight toward a diagnosis. When the script runs during the script development phase, the script development tool selects one of the diseases to consider next, and then selects one of that disease's symptoms to be considered next. Which disease and symptom is selected next depends on the Run Options that are selected by the author. The default sequence is the order in which the diseases and their symptoms are listed in this section.

DISEASE_NAME

The disease name is a unique label for a disease, used to identify the disease. It is only used internally and will never be seen by the patient.

ICD-9_CODE

A special code used by the medical profession to identify the disease.

FORMAL_TITLE

The formal title of the disease. The "formal" title is used here because common names for the disease, or acronyms, may be added in future formats.

SYMPTOM_NAME

The name of a symptom that is part of the diagnostic picture or "fingerprint" of the disease. The symptom is defined in detail in the Symptoms Section. In the DSQ list context, a "symptom" is a specific, detailed fact about the patient that has been assumed, asserted, elicited, or inferred. The author is free to define any data item(s) as a symptom. If it is useful to the author, symptoms may include non-medical facts such as name, rank, and serial number of the patient. The intent here is to give the author freedom to express his/her medical experience by defining elementary symptoms and grouping them in any convenient way.

To design a symptom, an author may imagine a set of weighted questions that would uniquely assert or deny the symptom. If this is no problem, the author defines the symptom (in the Symptom Section) in terms of its questions and answers. If the symptom turns out to be too complex, the author may break the symptom into parts, treat each part as a symptom, and ask questions about the part. The author may let the patient establish each part separately, and then use the inference mechanism of the Inference Section to establish the main symptom.

SYMPTOM_WEIGHT

The amount that this symptom adds to the disease's total score. Technically, the amount can be any number from −10,000 to +10,000; realistically it tends to be a small positive integer. As written, the script engine treats weights as a way to "score" a disease. When a symptom is established as being present in the patient, the script engine adds the weight of the symptom to the total score of the disease. When the disease score preferably reaches 1,000, the script engine rules the disease "in."

Simple arithmetic addition of weights may not express the specific way a symptom contributes or "indicates" the presence of disease. One solution for the author is to make a first guess of the weights, run the script, observe how the disease scores change with each question and answer, and then go back to "rebalance" the symptoms.

A "synergistic symptoms" technique may be useful to the author in developing a strategy for the weights. If there are two symptoms A and B that, if present together in a patient, carry more weight than each separately, then an artificial third symptom C can be defined that is implied by both A and B and adds extra weight to the disease. Symptom C has no associated questions; it is an internal "ghost" symptom that can be used only to add or subtract weights based on the presence or absence of other symptoms.

Symptoms Section

The Symptoms section lists and describes all of the symptoms mentioned in other parts of the script. For each symptom, this section identifies the Flow of questions used to elicit the symptom.

SYMPTOM_NAME

The symptom name is a unique label for a symptom, and is used to identify the symptom in other parts of the script. The name is only used internally, and will never be seen by the patient.

FLOW_NAME

The word "flow" is used to describe a specific set of weighted questions, asked in a specified sequence that can be drawn as a flowchart. Thus, a flow represents a single group of questions. Since one flow can elicit one of several symptoms, several symptoms will typically specify the same question flow to be used. Some symptoms (e.g., chief complaint symptoms) have no associated question flow.

Implications Section

The Implications section lists the logical inferences among symptoms, so that the script engine knows which symptoms imply other symptoms. Each line of the section specifies one or more symptoms that together imply another symptom. That is, each line gives the parameters for a logic formula of the form:

if symptom A and symptom B and symptom C then symptom D.

Symptom implications can be chained, so that one implied symptom can imply another symptom, alone or in conjunction with others.

One use of this section could be to establish "syndrome" symptoms, so that a specific set of symptoms in a patient would automatically assert a single, collective symptom. This combination symptom could also be used to add (or subtract) extra weight if a specific set of symptoms is present, i.e., to allow for the "synergy" of several symptoms present in the patient at the same time.

Flows Section

The Flows Section lists all flows in the script, and defines the sequence of questions and the symptoms that can be elicited by the flow. A "flow" is short for "a question flowchart". It can be thought of as a complex question that will establish one of several symptoms. Readers familiar with branch-based scripts will recognize that the flow can serve to contain or call an entire branch-based script that returns one of several response codes.

It is quite common that one needs to ask a patient several questions to elicit one specific symptom from the patient. For example, some preliminary questions ("Have you ever smoked?") may be needed to set the stage, followed by quite specific questions ("What is the total time, in years, that you smoked?) to define the patient's symptom precisely. One entire flow may contain 20 questions about smoking and may elicit one of several symptoms such as: has never smoked; is a casual smoker; has smoked 20-pack years and still smokes; and smoked 10-pack years, then quit 10 years ago.

Every node in a flowchart is encoded according to the path from node one of the flow taken to get to the node. These paths are used to identify what action should be taken at each node.

Questions Section

The Questions section defines the details of the questions mentioned by name in the Flows section. The details include the Preamble, the actual Question, the keys that can be pressed by the patient (on a telephone keypad), and (for graphic interfaces) the button label to be used for each answer.

PREAMBLE_TEXT

The Preamble is the text spoken or displayed to the patient before the question itself is asked. It may continue after a previous question, introduce a new subject, define some terms, and inform the patient why a question is about to be asked, and how to answer it. Only the name of the text is given here; the actual text is given in the Texts Section. If there is no preamble for a question, this is indicated with the digit zero as a place holder.

QUESTION_TEXT

The Question text is the actual question. Whereas the preamble may be 10 or 100 lines long, the question is typically short, to the point, and calls for a very specific answer that can be indicated by pressing or clicking one of the keys. Only the name of the question text is given here; the actual text is given in the Texts Section.

VALIDKEYS

A set of Valid Keys tells the script engine which keys the patient can press or click.

KEY1 . . . KEYN

These are key labels, used only in graphic display versions of the script. They tell the engine how to label each button, for example YES, NO, and NOT SURE.

Texts Section

The Texts section lists the actual text of all text items referenced by name in other sections, such as Preambles, Key Labels, and Question Texts. By giving each text a unique name, and listing the text in the Texts section, the author can use the same text in several places.

Having all of the text that is intended for the patient in one place also simplifies automated processing of the script, such as recording the text for use in a telephone network or formatting the text for display on a screen. A script could be translated into a foreign language, by replacing its Texts section text with the equivalent text in another language.

Description of Knowledge Capture Drawings

Figure 3A:
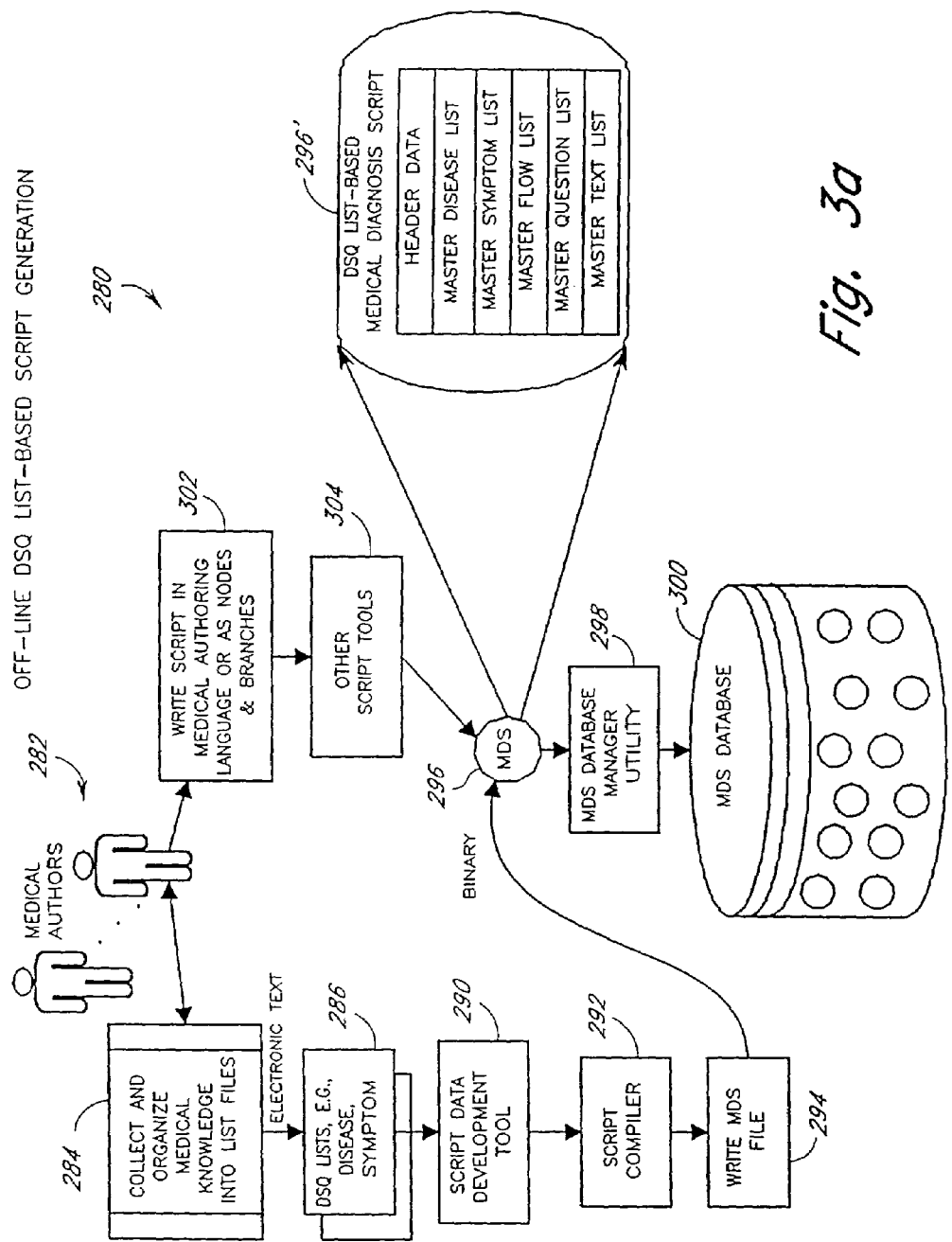
FIG. 3a; is a diagram of an off-line medical diagnosis script (MDS) generation process used in producing a script file for the MDS database shown in FIG. 2.

Referring to FIG. 3a, an off-line process 280 for generating a DSQ script will now be described. Beginning at a process 284, medical knowledge is collected and organized into list files. The data for the list files is collected for one or more medical authors 282. Process 284 has two portions. A first portion is typically performed by a script coordinator or supervising author for assigning diseases, and a second portion for capturing the disease knowledge for each disease in the script. The portion for capturing the disease knowledge is typically performed by a plurality of medical experts in their respective fields. The assigned diseases portion of process 284 will be further described in conjunction with FIG. 4a, and the captured disease knowledge portion of process 284 will be further described in conjunction with FIG. 4b. The output of process 284 is electronic text, such as an ASCII file. This electronic text is in the form of DSQ lists such as disease, symptom, and question lists 286. The Appendix includes an exemplary script for malaria. The script is one representation of a DSQ list.

Figure 3B:
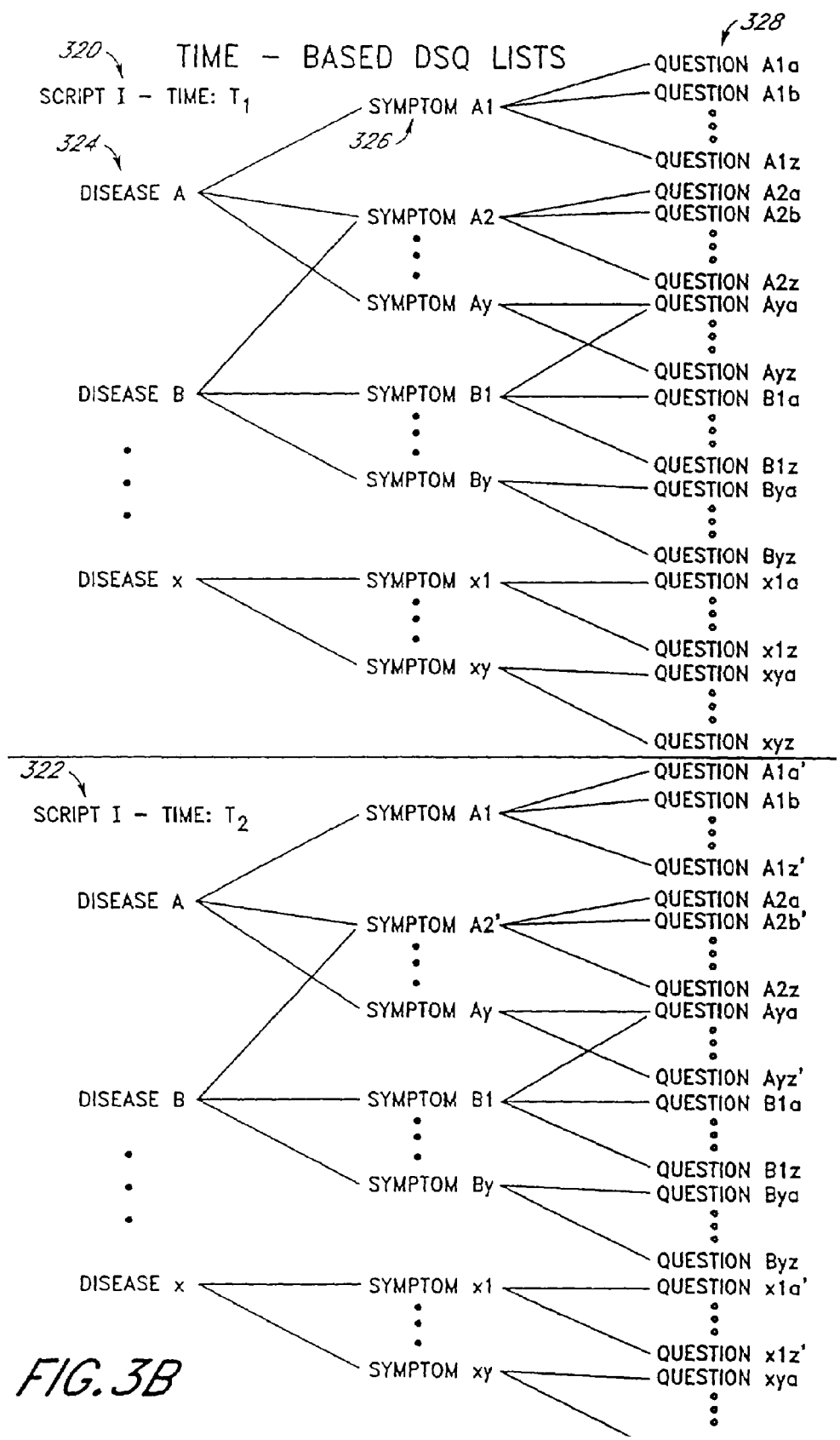
FIG. 3b is a diagram illustrating a possible hierarchy of the DSQ lists for a script at two different time intervals.

A graphical example of time-based DSQ lists for a script is shown in FIG. 3b. An exemplary script 320 for a time $T_1$ and a script 322 for a time $T_2$ are shown. Each of these two scripts includes a list of diseases 324, a list of symptoms 326, and a list of questions 328. This figure is intended to show the hierarchy of the disease, symptoms and question list, and is only exemplary. Note that a disease may refer to symptoms that are defined in other diseases, and a symptom may refer to questions that are defined in other symptoms. Thus, symptoms and their associated questions can be reused by the various medical authors.

Returning now to FIG. 3a, process 280 moves to state 290, which takes the DSQ lists in electronic text format and processes them by use of a script data development tool. A script compiler 292 works closely with the script data development tool to generate an MDS file. The process 280 may utilize the script data development tool and the script compiler in an iterative fashion to generate a final MDS file. At state 294, the MDS file is written to an MDS database 300 by an MDS database manager utility 298. The MDS file 296 is preferably in a binary format. In an exemplary representation of the MDS file shown in FIG. 3a at 296N, the MDS preferably includes a header data section, a master disease list section, a master system list section, a master flows section, a master question list section, and a master text list section. In another embodiment, the medical authors may write the scripts in a medical authoring language or as nodes and branches, as shown at state 302. Other script tools, which may include compilers, are shown at state 304 to generate an MDS 296.

Figure 4A:
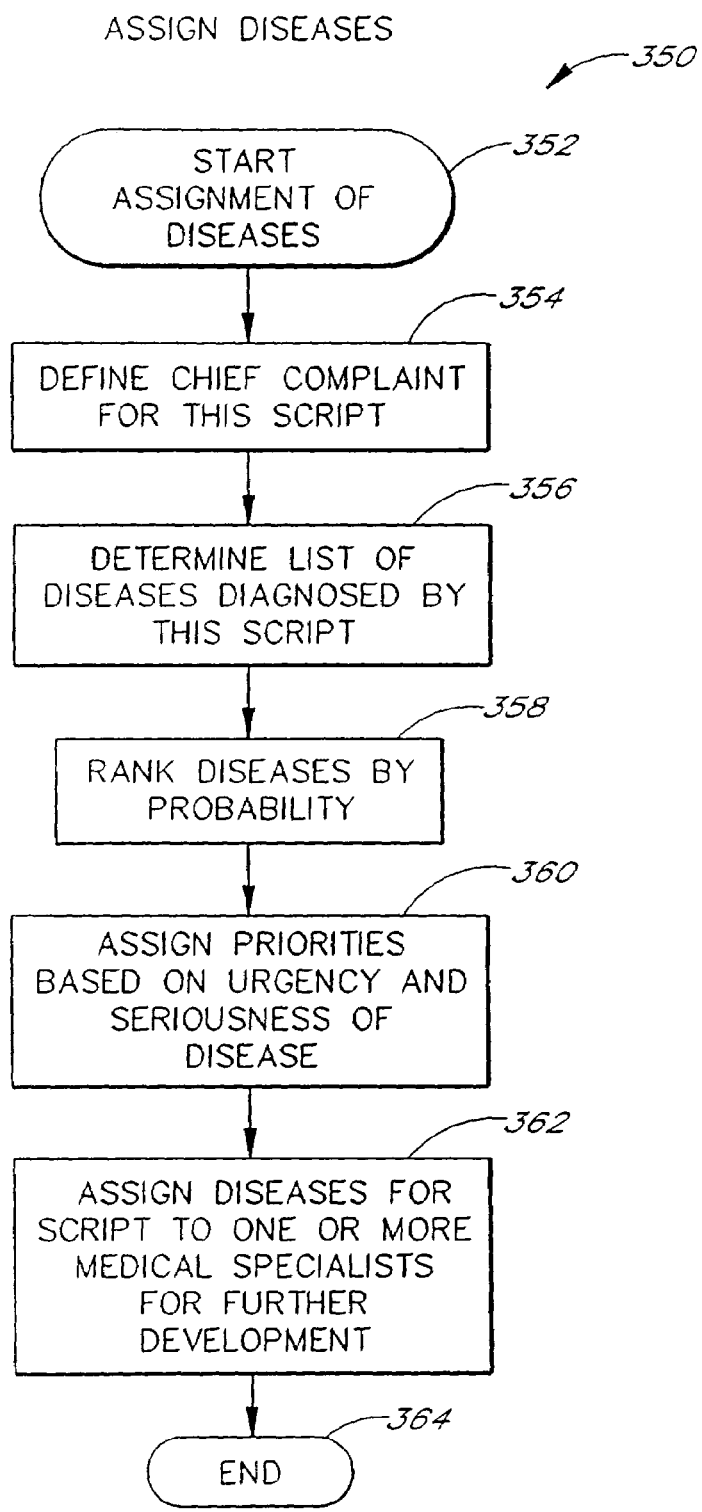

Referring now to FIG. 4a, the assign diseases process 350 of the collect and organize medical knowledge process 284 will now be described. Process 350 will typically be performed by a script coordinator, although other medical professionals utilized by the MDATA system may perform these tasks. Process 350 preferably is not performed by a computer but by the script coordinator, who may utilize the computer to assist in the completion of the following steps. Beginning at a start state 352, process 350 moves to a state 354, wherein the chief complaint associated with the current script is defined. The chief complaint includes the symptoms that a patient might initially provide to the system when describing the main problem that they are consulting for. Proceeding to state 356, the script coordinator determines a list of the diseases that are to be diagnosed by the current script. These diseases should provide a diagnosis of the chief complaint. Included in the list are the disease name, a descriptor, and an International Classification of Diseases (ICD-9) code for the disease. Advancing to state 358, the diseases are then ranked by probability of occurrence in the general population that the patient is in, e.g., country or region of a country. Moving to state 360, the script coordinator assigns priorities to the diseases based on urgency and/or seriousness of the disease. Based on the assigned priorities, the script engine may be directed to check first the diseases that have an urgent or serious indication assigned to them. Continuing at state 362, the script coordinator then partitions or assigns the diseases for the current script to one or more medical specialists for further development. Using a computer network, such as the Internet, and a DSQ lists database, multiple scripts can be developed in parallel. The disease authors can work in parallel by making questions and instructions available to all the other authors via the database and the network. This capability allows rapid development of the scripts. Process 350 ends at an end state 364.

Figure 4B:
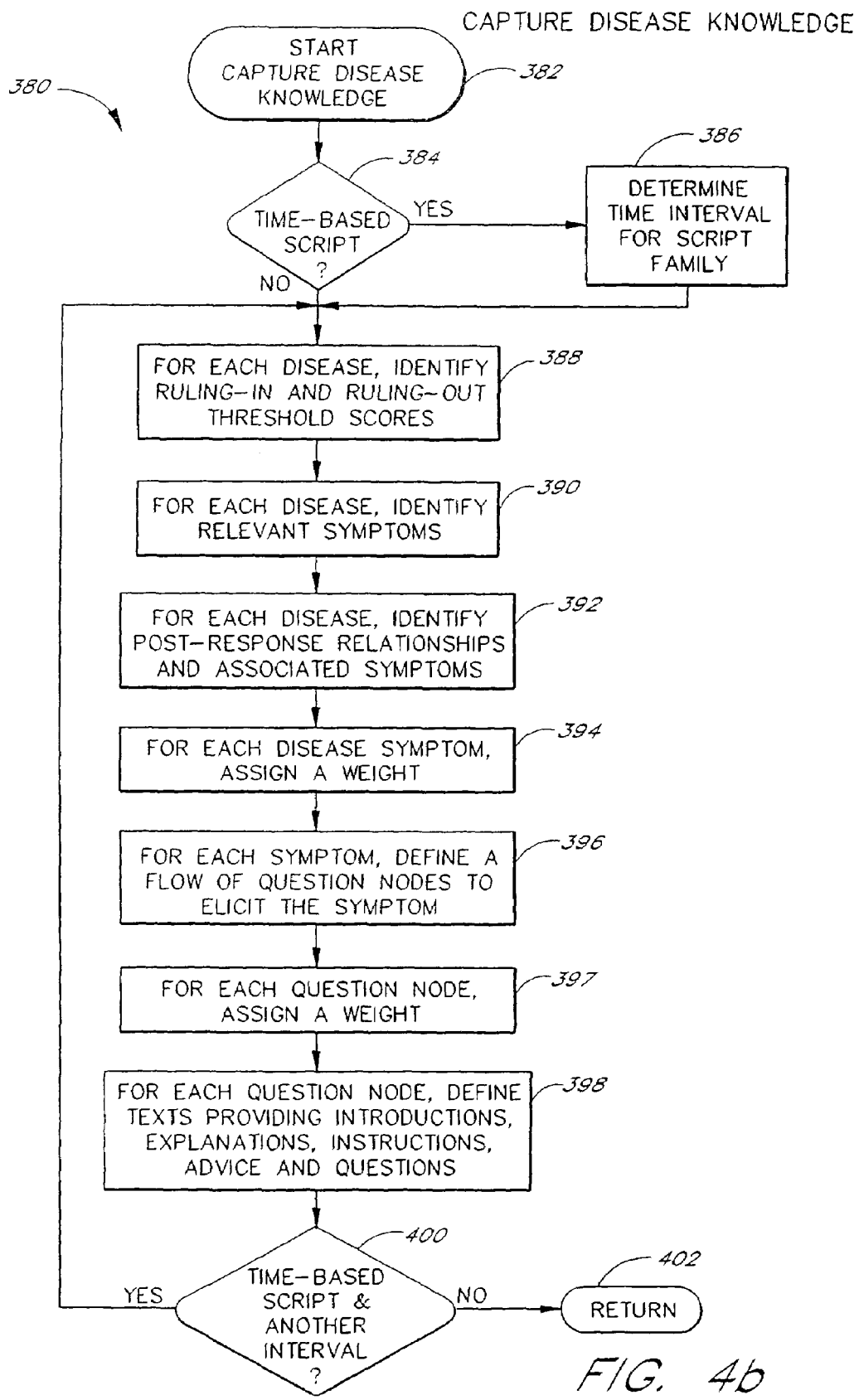

Referring now to FIG. 4b, the capture disease knowledge portion 380 of the collect and organize medical knowledge process 284 will now be described. Process 380 is also not typically performed by a computer, but is performed by a medical specialist or expert who may employ the use of a computer to actually capture the disease knowledge for a particular disease. The following steps are performed by the disease specialist, as assigned by the script coordinator at state 362 in FIG. 4a.

Beginning at a start state 382, process 380 moves to a decision state 384, wherein the medical specialist determines if the script is best captured as a time-based script. That is, a plurality of scripts at sequential time intervals, forming a script family, are to be generated to track the diseases over time. If it is determined to be a time-based script, process 380 moves to state 386, wherein the time interval between scripts in the script family is determined. For example, the script author may decide to generate a script for every two hours for a 48-hour time period. At the completion of determining the time interval for the script family, or if the script is best shown as a single script, process 380 continues at state 388, wherein the medical specialist identifies a ruling-in threshold score and a ruling-out threshold score for each disease that is assigned to him or her. Moving to state 390, the medical specialist identifies a set of relevant symptoms for each disease assigned to them. The symptom list includes the symptom name, a descriptor, and at least one weight as described hereinbelow. Continuing at state 392, the medical specialist identifies any relevant post-response relationships and symptoms identified by these relationships. The post-response relationships may include simultaneous or synergistic relationships where two or more symptoms occurring together may have more weight toward diagnosing a disease than the sum of the weights for the symptoms occurring separately. A sequential relationship is where the symptoms occur one after the other, which may produce more weight toward diagnosing a disease then the sum of the weights of the individual symptoms occurring separately. A variation of the sequential relationship is wherein the sequence of the onset or ending of the symptoms produces a different weight than the symptoms do alone. Implied relationships are wherein the presence of one symptom implies the presence of another symptom. The medical author may also define relationships over time for the asserted symptoms and further post-response processed symptoms. The post-response relationships may also involve symptom clarification processing, PQRST array analysis, or a symptom severity clarification. The PQRST array is an N-dimensional array with different attributes or aspects of the symptom of pain assigned to one dimension. For example, the PQRST array may have twenty-two dimensions.

Proceeding to state 394, the medical specialist assigns a weight for each disease symptom. For symptoms having an associated range, such as a severity of pain or other type of symptom severity, the medical specialist may assign a range of weights associated with the severity of the symptom. Symptom weights are accumulated into a score for each disease having the symptom. Weights can be either positive or negative, which contributes to the production of a positive or negative score. Moving to state 396, for each symptom, the medical specialist defines a flow of question nodes to elicit or determine the symptom. Some symptoms can be determined by a single question, but most symptoms may require a number of questions to elicit the symptom. For the symptoms requiring a plurality of questions, weights are assigned to the possible responses of the questions at state 397. Thus, this type of symptom may have a range of associated weights. Advancing to state 398, for each question node of the question flow, the medical specialist writes text objects for the question node so as to provide an introduction or an explanation, instructions, advice and the actual questions for the patient. The instructions may define the range of values that are requested (an answer set) or other ways of formatting the expected responses. The introductions and explanations are to help the patient understand what the question is about, why the question is being asked, and sets the stage for the possible responses.

For each symptom the author will compose a question flow that is used to elicit the symptom. The question flow that the author uses may be another physician's question flow. For example, let's say the symptom is depression. To establish the symptom of depression, one doctor may ask, "Are you depressed?". This might be called depression_question_1. Let's say that the author does not like it. It is too terse and really does not capture what is wanted. So the author looks further in the question database. The author may find and look at depression_question_flow_2. This question flow is much more elaborate. In this flow, to answer the question, "Are you depressed?", this doctor has devised a 10-point list of questions. The sub-questions may even be other questions in the database. In this question flow, the patient is asked ten questions. Each question is weighted differently and, after answering all of the questions, the score is totaled, and if it reaches a threshold defined by the question's author, then this physician will say that the patient has the symptom of depression.

In another example, say an author wants to ask a question about nausea for migraine. The author examines the question bank. The author may find fifty different questions on nausea. One question says, "Are you nauseated?". This question is not acceptable to the migraine author. Another author has a question flow that contains ten weighted sub-questions. If their score reaches that author's pre-defined threshold, that doctor calls his patient nauseated. The migraine author likes it almost as is, but wants to change one of the weights of one of the weighted sub-questions. In this situation, the migraine author saves the new question with the revised weight as nausea_question_n+1. Now when the migraine author uses the new version or another version of nausea, it will of course be weighted differently in defining different diseases.

If questions of different weights are not allowed in the question flows, then all the questions will be, by definition, weighted the same. But when a disease author, trying to see if, say, abdominal tenderness is present, will ask the patient to do a series of maneuvers such as: "Please cough. Does that make your abdomen hurt?" If the patient says "yes", the disease author may then ask the patient to press on his abdomen and ask if that hurts. The disease author usually asks or requests the patient to perform many such maneuvers to establish the "symptom" of abdominal tenderness. However, these questions are not all of equal importance in defining abdominal tenderness. If a patient hurts when his abdomen is pushed, that is much more significant than the coughing maneuver.

After the question nodes have been completed at state 398, a medical specialist determines at a decision state 400 if another time interval for a time-based script is required. If another interval is not required or if the present script is not a time-based script, process 380 ends at a return state 402. However, if another interval is required in a time-based script, process 380 moves back to 388 to rerun the set of steps 388 to 400 for another time interval in the script family.

IV. Script Generation Details

Internal to the MDATA system, list-based medical diagnosis data is stored as scripts. These files are the diagnostic interface between the human doctor and the patient being interviewed. At run time, a MDS file "runs" by driving a script engine, which is a generic program that loads MDS files and runs the script based on the data and instructions encoded in the file. Diagnostic data are stored in the form of disease, symptom, question, and text node lists.

The contents of a list-oriented MDS file mirrors the contents of the ASCII list file. The major difference between them is that the text file data is stored as segments of text lines of character strings, whereas the MDS file data is packed into lists of binary integers. A second difference is that the MDS file data is arranged and cross-referenced to support on-line access to the data.

The MDS file is preferably formatted as one very large array of 32-bit binary integers. This large array is then allocated into blocks of varying length that contain data. Since the location of a block in the file is itself a number, it can be used as a data item that connects one block to another block. Physically, these blocks are independent of any programming language or operating system and can be transported to any computer hardware that is capable of storing files of 32-bit numbers. Logically, these blocks can be nested and connected in arbitrary ways to form data structures such as linked lists, stacks, queues, trees, and networks. The MDS file is formatted as several segment blocks called "master lists" as follows:

Header Data,
Master Disease List,
Master Flow List,
Master Question List,
Master Symptom List,
Master Text List.

To prepare a MDS file, the ASCII list file is read and converted into a MDS file by the script compiler. This process consists of reading the ASCII text file line-by-line, compiling the appropriate segment of the corresponding MDS output file, and generating cross-reference lists to speed searches. Since some symbols may be used before they are defined, the conversion program must make two passes through the file. During the first pass, all lines are read in, converted into MDS file blocks, and their symbols are saved in a table. During the second pass, symbols are replaced by their actual block addresses. Of course, other methods of compilation may be used.

The conversion program can, of course, perform any number of quality and consistency checks, such as detecting invalid formats, missing segments, duplicate symbols, unused symbols, typographical errors and so on. Coupled with a simple text editor, the conversion program can let the script author make corrections in the ASCII list file and then rerun the conversion program again until it accepts the file. This editing cycle serves to catch fundamental source errors and typographical errors early.

After the script is compiled, the script author tests the script to determine whether it functions as intended. If not, the script author may, for example, adjust symptom/question weights, fine-tune words and phrases for the question nodes, and fix any logical and medical errors. The script author will then recompile and rerun the script until it runs as intended.

Figure 5:
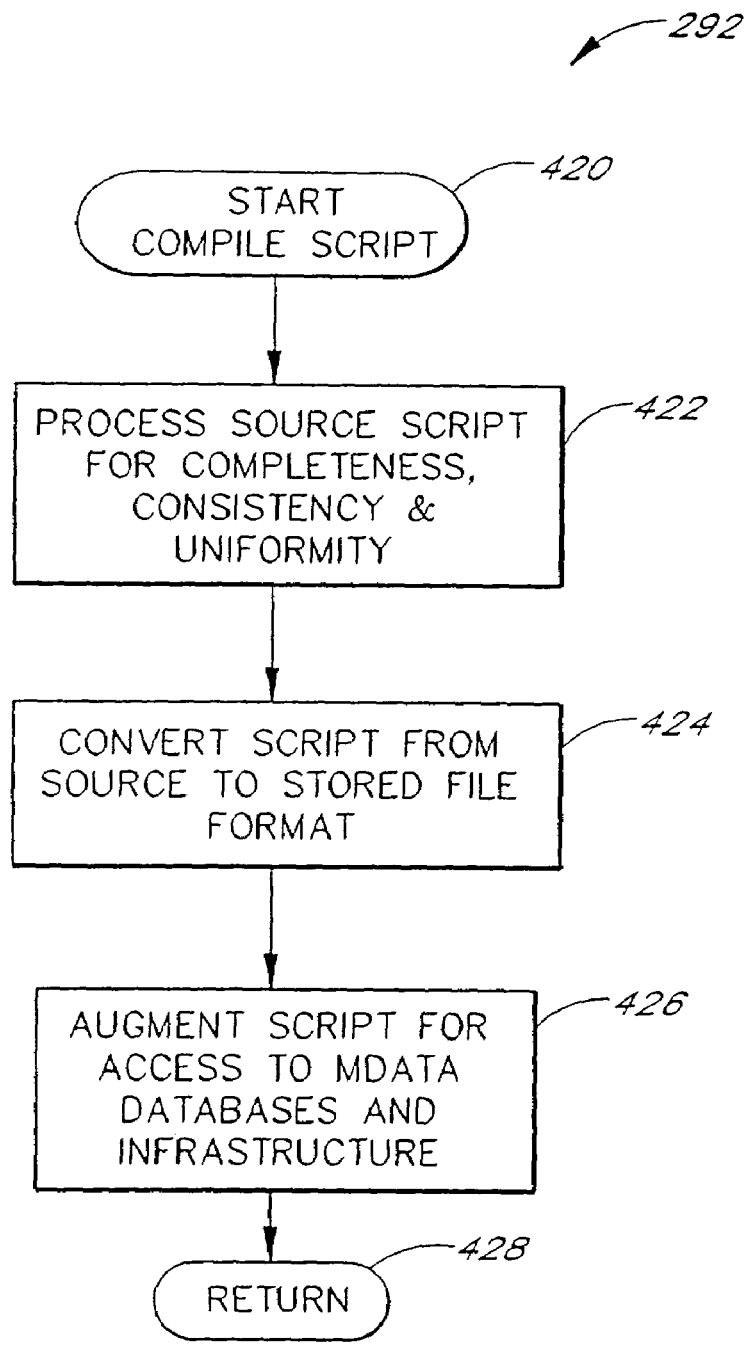

Referring to FIG. 5, the script compiler 292 will now be described. The DSQ lists that are in an electronic text format, such as ASCII, are collected by use of the script data development tool and then processed by the script compiler 292. Beginning at a start state 420, the script compiler processes the source script for completeness, consistency and uniformity. Syntax errors are identified at this state. After any problem areas are corrected, the compiler proceeds to state 424 and converts the script from the source format to the stored file format, which is a binary format. Continuing at state 426, the script compiler 292 augments the script for access to the various MDATA databases, shown in FIG. 2, and the MDATA infrastructure or support system. The script compiler completes at a return state 428.

V. Script Execution Details

Overview

When a patient accesses the MDATA system 100 for a diagnosis, the system manages the initial contact with the patient, identifies the patient, decides which service the patient needs, selects the correct MDS file, and starts up the script engine. The script engine loads the MDS file and begins to obey its coded directions, one by one. The effect of obeying the coded directions is an interview with the patient. At the end of the interview, the script directs the engine to perform appropriate terminal actions (updating databases, closing files, logging the session) and ultimately returns computer control to the MDATA system 100.

Using an MDS file to drive a script engine to conduct an on-line interview is described hereinbelow. The supporting operations required to access database files, output information to the patient, input the patient's responses, and print reports, is performed by the underlying operating system on which the script engine is running.

The run-time mode of the List-Based Processing method generates a MDS file that is list-oriented. That means that, at each step, the disease, symptom, and question lists must be searched to determine the next question or action of the script. The script engine has to do more work using the list-based method than a branch-based method.

The MDS file is, in essence, a medical encyclopedia of human diseases, stored in top-down order from a high-level list of diseases down to a single question that elicits one aspect of a symptom of one disease. To run such a data structure as a script requires that the structure be "inverted," i.e., presented as a sequential question stream to the patient. To do this in the run-time mode, the script engine first searches the master disease list of the MDS file to select the next disease to be considered. Then the engine searches the list of symptoms of the selected disease to select the next symptom to ask about. Then the engine searches the question set for the selected symptom to select the next question to be asked. The engine poses the question to the patient, obtains the answer, updates the various weighted lists, and repeats the process until it reaches a diagnosis or runs out of diseases. The overall effect is to generate a diagnostic conversation between the script and the patient that concludes with a diagnosis.

As the script runs, the script maintains the patient's symptom set as a temporary dynamic list called a "temp" list. Every new symptom is recorded in this set, and is used to update the list of diseases being considered. The patient's responses thus build a health profile that is used to select the next disease and symptom and question. The profile serves a number of uses:

it is used to update all diseases being considered, to aid in selecting the next disease;
    it can be used to make statistical comparisons of cases;
    it allows the MDATA system to dynamically alter the question stream based on a specific patient's health state;
    it allows the MDATA system to interrupt a script and to continue it later, by storing the profile and reloading it at a later time to continue the script.

When the script engine begins, it is given an on-line patient and a script (i.e., a MDS file). The engine opens the MDS file to establish access to the coded lists of diseases, symptoms, and questions. It also opens the patient record to obtain the patient's medical history and the results of past sessions, if any, with the patient. From hereinforward, the MDS file drives the interview by directing the engine to a next interview step. At the end of the interview, the script directs the engine to perform appropriate terminal actions (updating databases, closing files, logging the session) and ultimately returns computer control to the MDATA system.

The aspect of interest for this explanation of List-Based Processing is the algorithm used to question the patient and to build up a set of symptoms toward a diagnosis. This algorithm consists of a main loop that analyzes and updates a set of patient symptoms until it reaches some condition that terminates the loop. The main loop includes the following general steps:

analyze the patient's set of symptoms,
    select the disease to be considered next,
    select the symptom to be considered next,
    select the question to be presented next,
    present the question to the patient and process the response,
    update the symptom set based on the response,
    perform post-response processing of the symptom set,
    loop to analyze the patient's set of symptoms.

This main loop continues until the script terminates with some exit action such as forming a diagnosis, giving treatment advice, or forwarding the patient to another script.

Description of the Script Execution Drawings

Figure 6A:
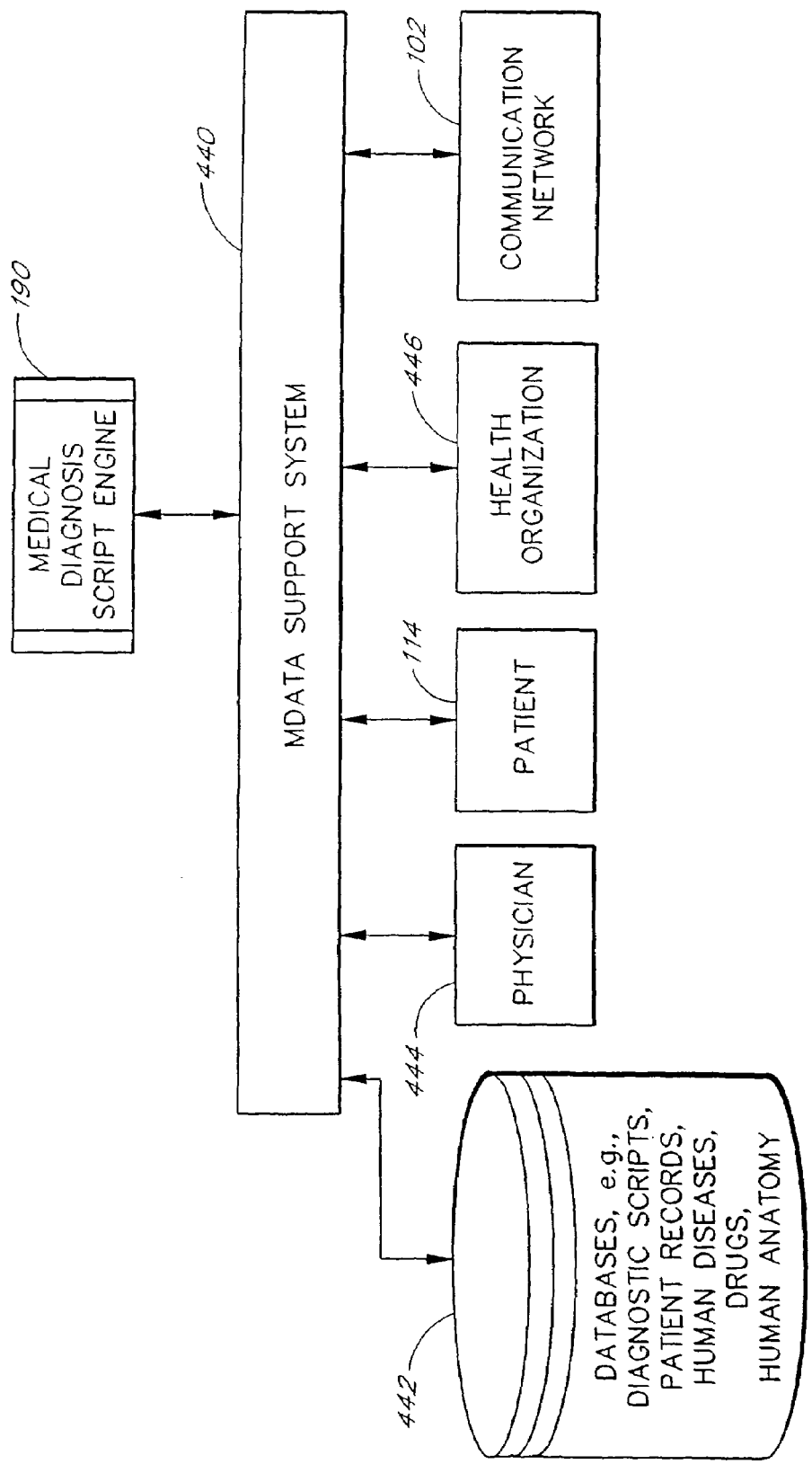
FIG. 6a is a block diagram showing a configuration used during operation of the diagnostic script engine.

Referring now to FIG. 6a, a general configuration of the MDATA system for operating the diagnostic script engine 190 will now be described. The diagnostic script engine 190 interfaces with a MDATA support system 440 so as to get access to a plurality of databases 442 of the MDATA system and to have input and output capabilities with the various entities in the medical community. The MDATA support system 440 includes the processes shown in FIG. 2, including the login process 210, the registration process 212, and the diagnostic process 220. Also included in the MDATA support system 440 are processes for performing input and output to and from the physician 444, the patient 114, and health organizations 446, such as a health maintenance organization (HMO). The MDATA support system 440 utilizes the communication network 102, previously shown in FIGS. 1a and 1b. The databases 442 shown in FIG. 6a include the databases previously shown in FIG. 2 and also include other databases such as for human diseases, drugs and drug interactions, human anatomy, a regulatory ratchet table, and a geographic distribution of frequency of diseases. The regulatory ratchet table is a table of regulatory and legal "rules" that let the system know how much information can be revealed to a patient.

Figure 6B:
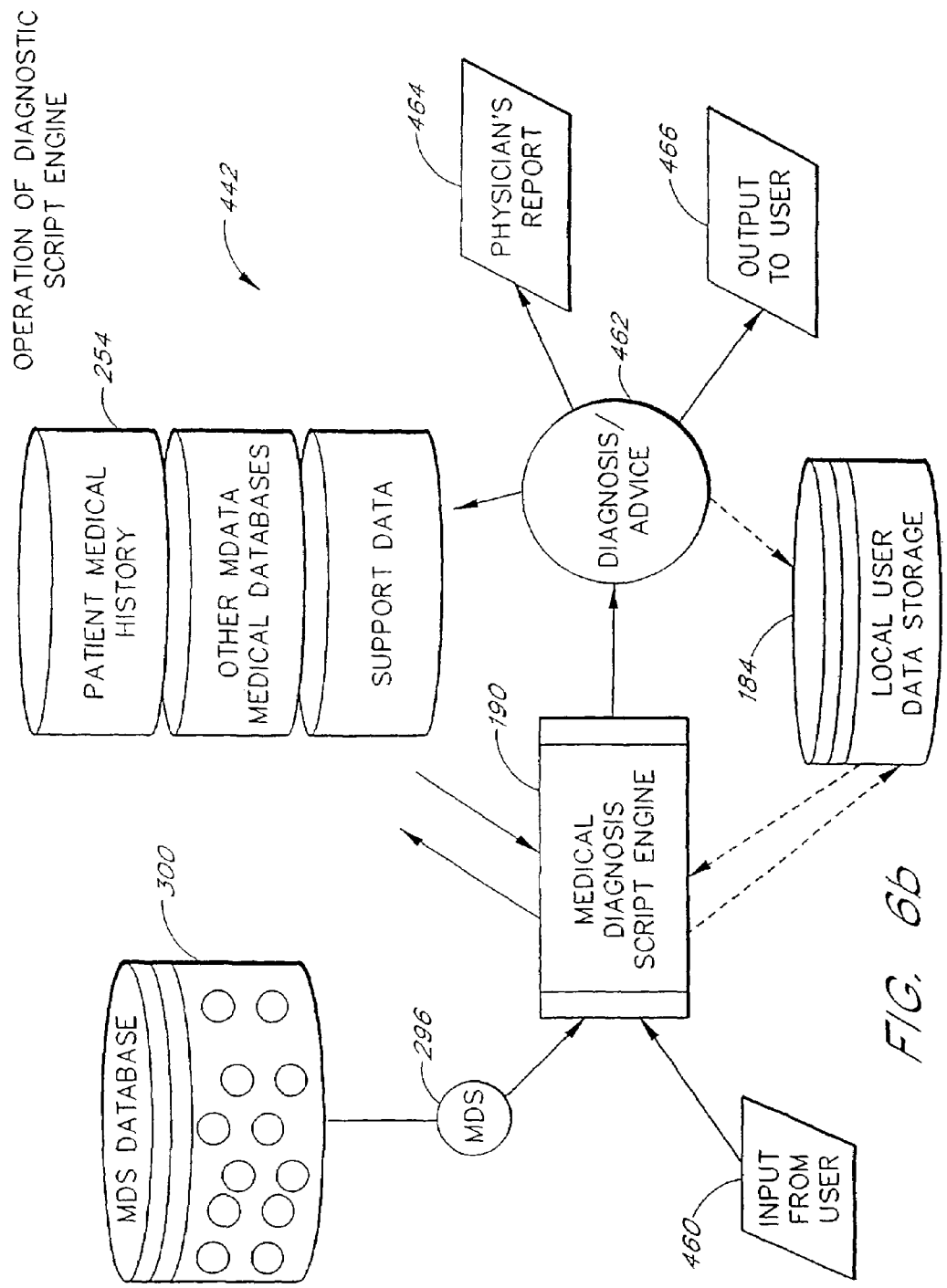
FIG. 6b is a block diagram showing a set of structures and inputs used during operation of the script engine and the outputs produced by the MDATA system.

Referring now to FIG. 6b, the structures and inputs and outputs utilized during the operation of the diagnostic script engine will now be described. Based on input from user 460, records from the patient medical history database 254 and other information available from the central MDATA databases 442, a MDS 296 is selected from the MDS database 300. Alternatively, if the diagnostic script engine 190 is run on a patient's personal computer, local user data storage 184 may be accessed in place of the MDATA databases stored at a central location. However, it is more practical to keep the patient medical history at a central database for several reasons: safety of the records, health care providers anywhere in the world have access as necessary for analysis, matching a diagnosis to any new treatments so that a patient can be quickly notified by the system, and so forth.

The MDS 296 is made available for the diagnostic script engine 190, which performs the patient interview. The script engine 190 may write information received during the patient interview to either the central patient medical history database 254 or to the local user data storage 184. At the conclusion of the current script, or if additional scripts are run, medical diagnosis or advice 462 may be generated. This diagnosis or advice is preferably reported to the physician 464, output to the user 466 and stored in the central MDATA databases or the local user data storage 184. Other reports 468 may be generated as necessary. As will be described later, there are situations where the diagnosis may not be reported directly to the user, but may be sent instead to the physician for further reporting to the user at a later time.

Figure 7:
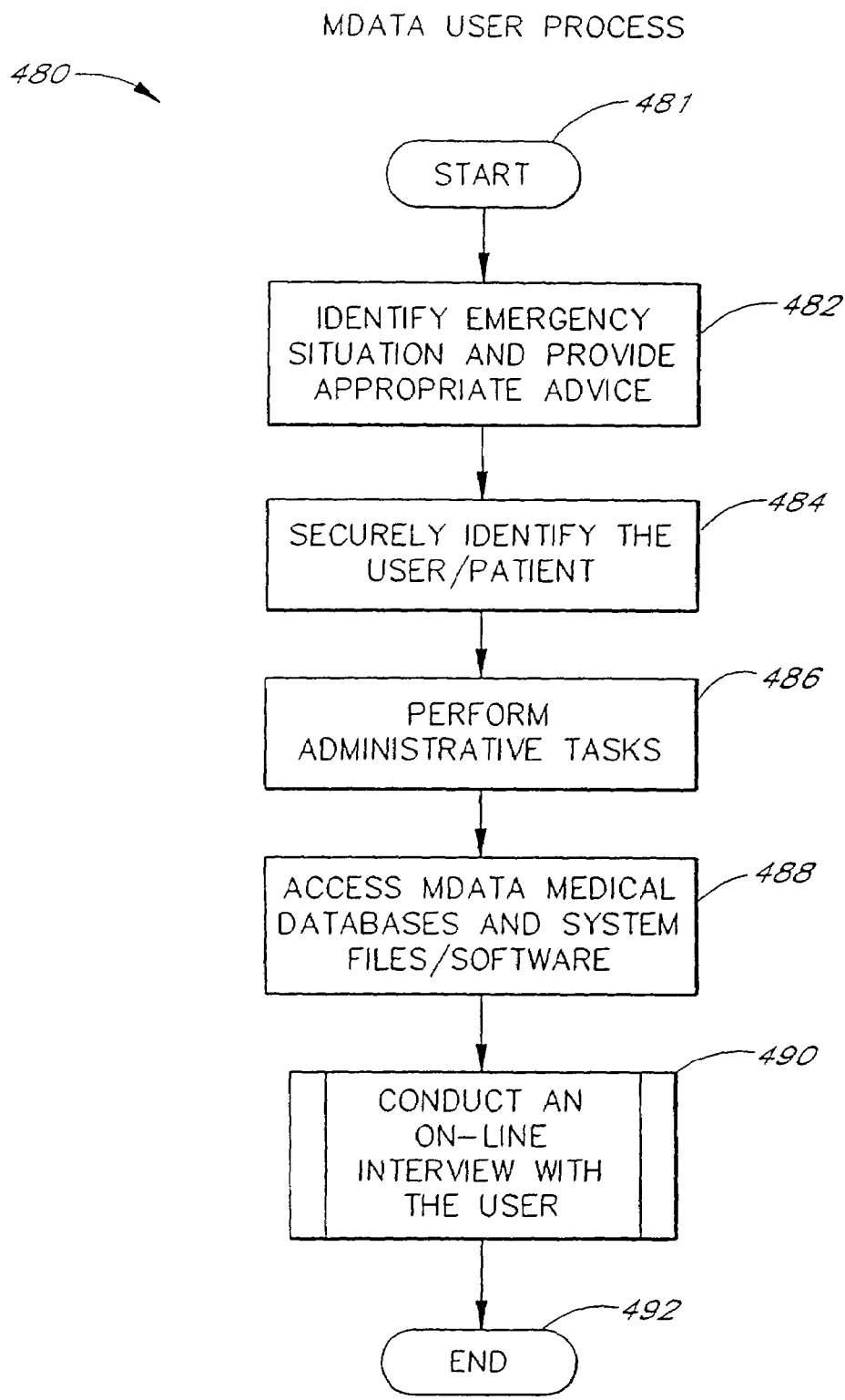
FIG. 7 is a top-level flow diagram of a user process for the MDATA system of FIG. 1.

Referring to FIG. 7, a general top level process 480 for a user in a session with the MDATA system 100 will now be described. Process 480 begins at a start state 481 and moves to state 482 to identify an emergency situation. A set of initial "hard-coded" screening questions are utilized to identify the emergency situation. If an emergency situation is identified, appropriate advice, such as calling 911, is provided to the user. State 482 and subsequent states 484, 486 and 488 are substantially described in Applicant's application entitled "COMPUTERIZED MEDICAL DIAGNOSTIC AND TREATMENT ADVICE SYSTEM," U.S. Ser. No. 08/176,041, now U.S. Pat. No. 5,660,176. If process 480 determines that there is no emergency situation, the process continues at state 484 and securely identifies the user. As described in Applicant's U.S. Pat. No. 5,660,176, the user may be the patient or an assistant for the patient. Passwords, identification numbers, voice prints or other types of identification methods may be utilized. If the patient has logged in properly, process 480 continues at a state 486 to perform any necessary administrative tasks. Proceeding to state 488, process 480 access the MDATA medical databases (FIG. 2) and the system files and software. Proceeding to process 490, an on-line interview with the user is conducted. The on-line interview preferably is performed by the diagnostic script engine process 490. However, other ways of performing the on-line interview may be utilized, such as running a program or executing a script. The user process 480 completes at an end state 492.

Figure 8A:
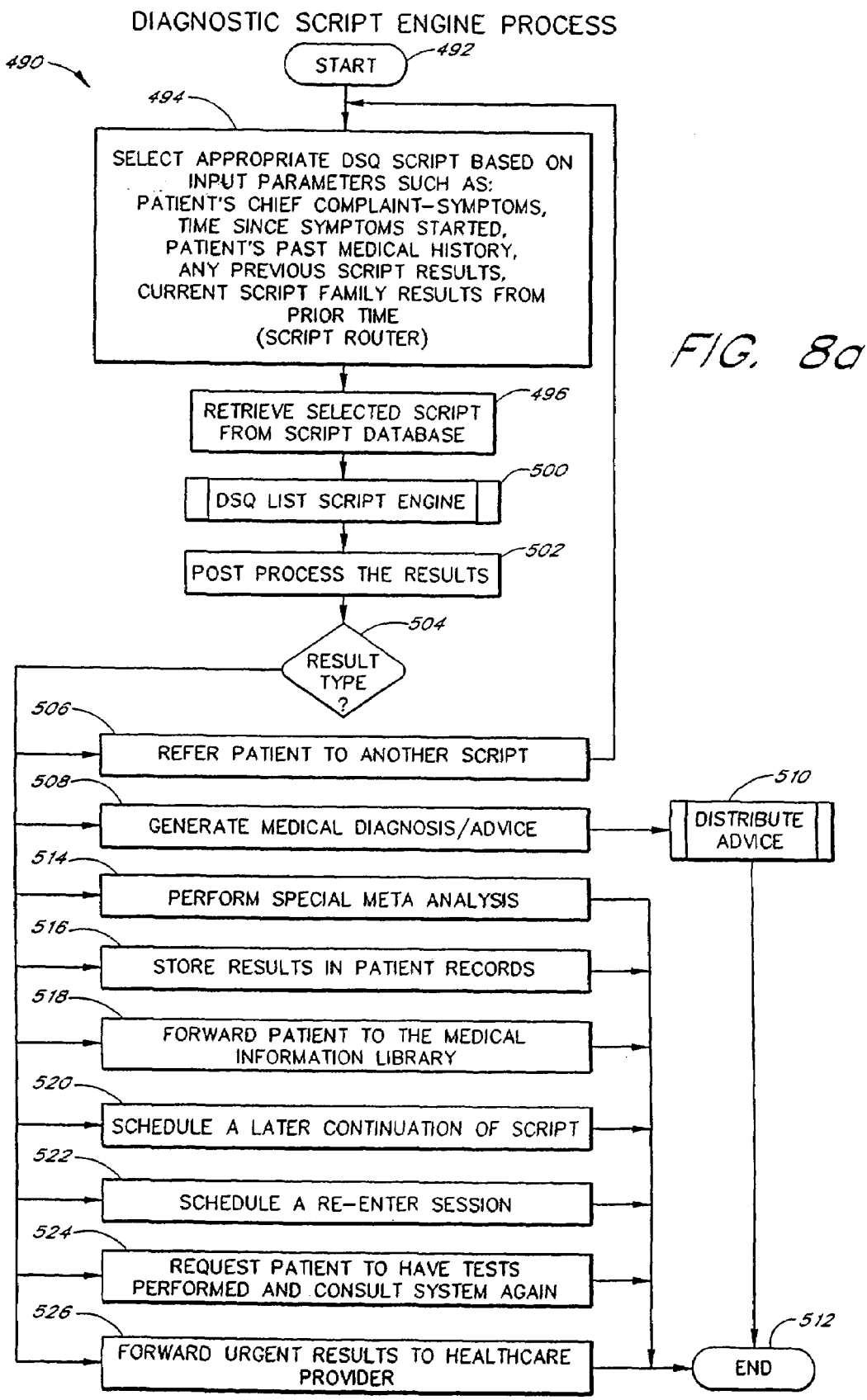
FIG. 8a is a flow diagram of the "diagnostic script engine" process used in performing the on-line interview process shown in FIG. 7.

Referring now to FIG. 8a, the diagnostic script engine process 490 will be described. Beginning at a start state 492, the script engine process 490 proceeds to state 494 to perform a script router function. The script router selects an appropriate DSQ script based on input parameters such as: a patient's chief complaint symptoms, the time since the symptoms started, the patient's past medical history, results from any other scripts, or the results from the current script family from a prior time. Identification of the patient's chief complaint is algorithmic. The chief complaints can be categorized into the following classifications: an anatomic system involved, a cause of the patient's problem, e.g., trauma or infection, an alphabetic list of chief complaints, an ICD-9 number for their complaint, or a MDATA catalog number of their chief complaint. After the appropriate DSQ script has been selected, process 490 continues at state 496 to retrieve the selected script from the script database 300 (FIG. 6b). At this time, the diagnostic script engine process 490 invokes a DSQ list script engine 500 to utilize the DSQ lists in performing the interview with the patient. The DSQ list script engine 500 will be further described in conjunction with FIGS. 9 and 11.

The diagnostic script engine process 490 post-processes the results of the DSQ script engine at state 502. Various types of processing are performed at state 502, as exemplified by states 506 through 526 described hereinbelow. One action that may be performed at state 502 includes determining a degree of certainty for diseases in the ruled-in disease list and in the ruled-out disease list. The degree of certainty for some or all the diagnoses in the ruled-in and ruled-out disease lists may be reported to the patient and/or physician. The diagnoses from the ruled-in and ruled-out disease lists and the associated degrees of certainty are compiled into a differential diagnosis list. Various ways of determining the degree of certainty for a diagnosis include, for example, a degree of certainty look-up table or a sensitivity factor set. Sensitivity factors were previously described in Applicant's issued patent, U.S. Pat. No. 5,594,638, entitled "COMPUTERIZED MEDICAL DIAGNOSTIC SYSTEM INCLUDING RE-ENTER FUNCTION AND SENSITIVITY FACTORS." The next action performed by process 490 is dependent on the result type as determined at a decision state 504. Various exemplary result types will now be described. At state 506, the diagnostic script engine process 490 refers the patient to another script, which is selected at state 494, as previously described. At state 508, process 490 generates appropriate medical diagnosis or advice. Moving to function 510, the advice is distributed to the appropriate party. Function 510 will be further described in conjunction with FIG. 8b. After the advice is distributed, process 490 ends at an end state 512.

At state 514, process 490 performs a special meta analysis. The diagnostic script engine studies how a specific symptom changes or grows over time in a given disease. At state 516, process 490 stores the results accumulated during the script into the patient's records. At state 518, process 490 forwards the patient to access a medical information library that is part of the MDATA system 100. At state 520, process 490 schedules a later continuation of a script that was adjourned temporarily. Typically, this occurs when a patient is not able to complete the entire script during a session. In a situation where no disease has reached a rule-in threshold, the diagnostic script engine has the capability of providing a list of diseases that have the most weight in decreasing levels of probability to the patient. In such a situation, at state 522, the process 490 could schedule a re-enter session to allow a length of time to pass and see if a diagnosis could be reached at a later time. The re-enter feature is described in Applicant's application entitled "COMPUTERIZED MEDICAL DIAGNOSTIC AND TREATMENT ADVICE SYSTEM." At state 524, process 490 requests the patient to have tests performed and to consult the system again. These tests may include self-exam maneuvers, imaging modality tests (258, FIG. 2) or laboratory tests (260, FIG. 2). At state 526, process 490 forwards any urgent results to a health care provider for immediate action. Process 490 ends at the end state 512.

Figure 8B:
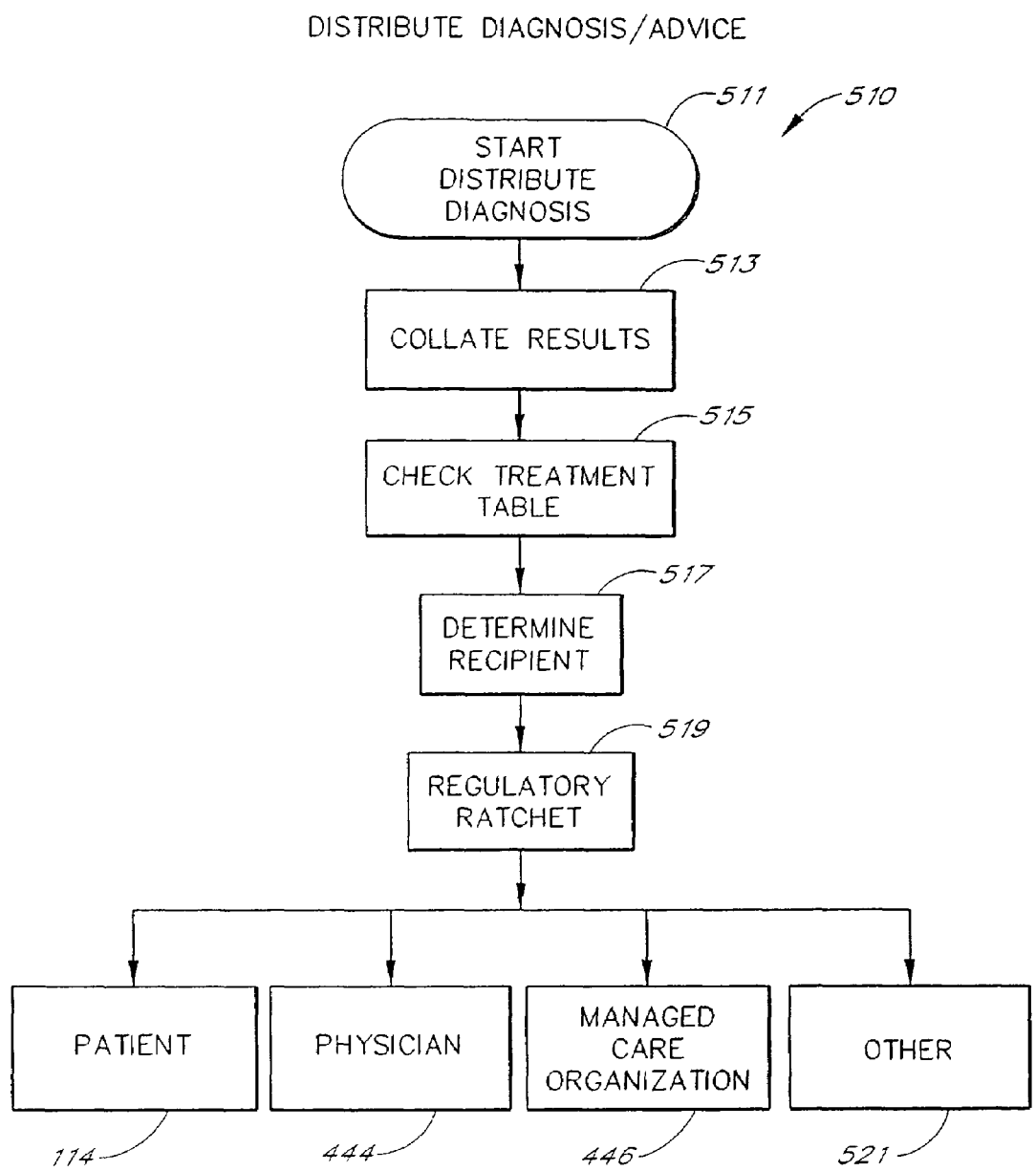

Referring to FIG. 8*b*, the distribute diagnosis or advice function 510 will now be described. Beginning at a start state 511, function 510 proceeds to state 512 wherein the results of the various lists are collated due to one or more diseases or diagnoses reaching threshold. Proceeding to state 515, function 510 checks the treatment table for the appropriate and current treatment for the diagnoses made by the system. Proceeding to state 517, function 510 determines who should be the recipient of the diagnosis or advice. This is partially accomplished by consulting a regulatory ratchet table 519. The regulatory ratchet table determines the type of information that can be told to the patient depending on various factors, such as what country the patient lives in. As a result of consulting the regulatory ratchet table 519, advice or a diagnosis is communicated to the patient 114, a physician 444, a managed care organization 446 or other entity 521 that legally may have access or has a need to know the medical information. There is much information that could be shared with the patient and should be shared with the patient's physician. For example, what is ruled in and what is ruled out, and what is the patient's specific differential diagnosis? That is, after the patient answers all of the questions, the scores for all of the different diseases can be ranked. This is very helpful to the physician. The regulatory ratchet table 519 utilizes information available in the patient's record, such as the patient's zip code or telephone area code to identify their location.

Figure 9:
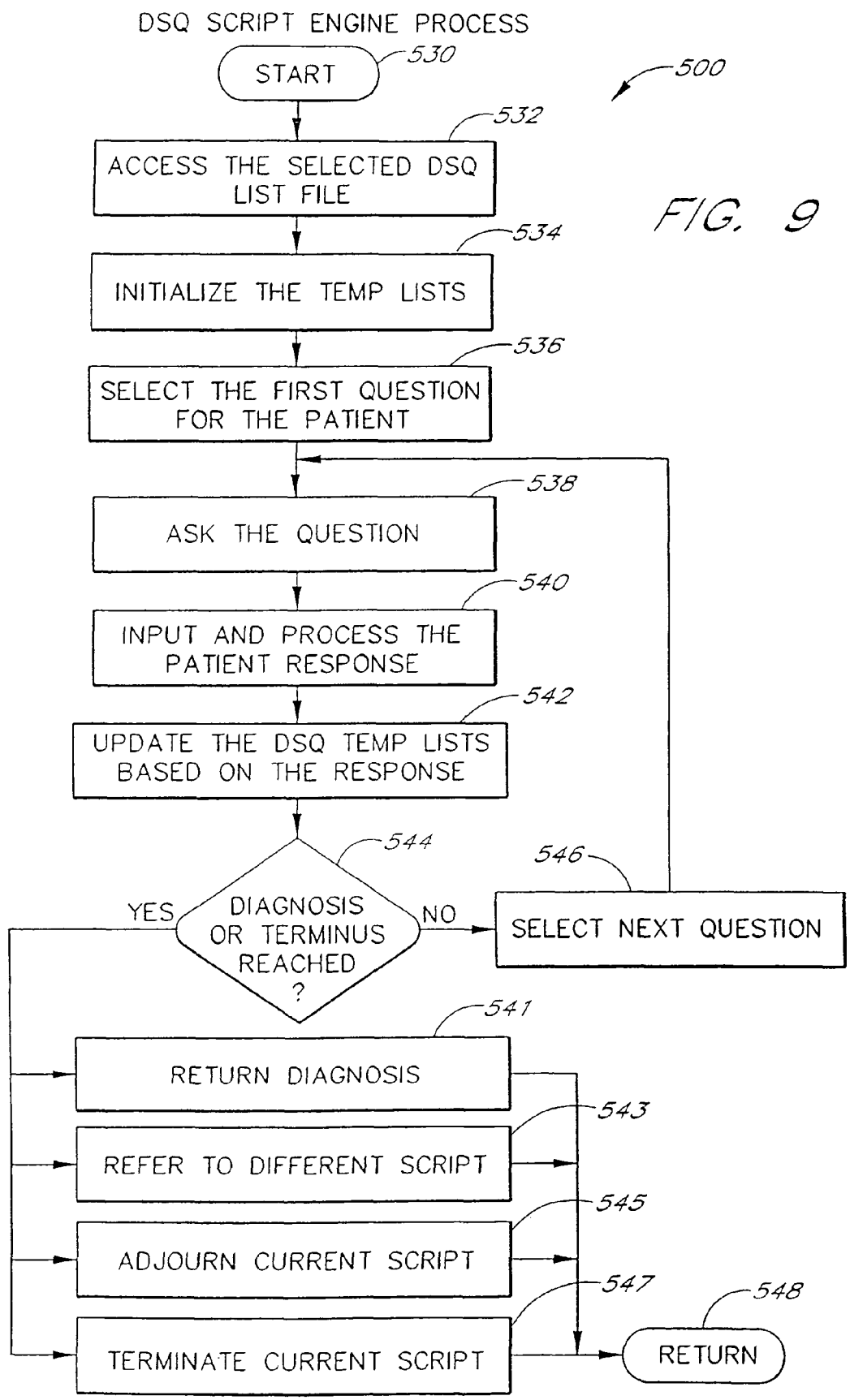
FIG. 9 is a flow diagram of portions of the "DSQ list script engine" process shown in FIG. 8a for list-based processing.
Figure 10:
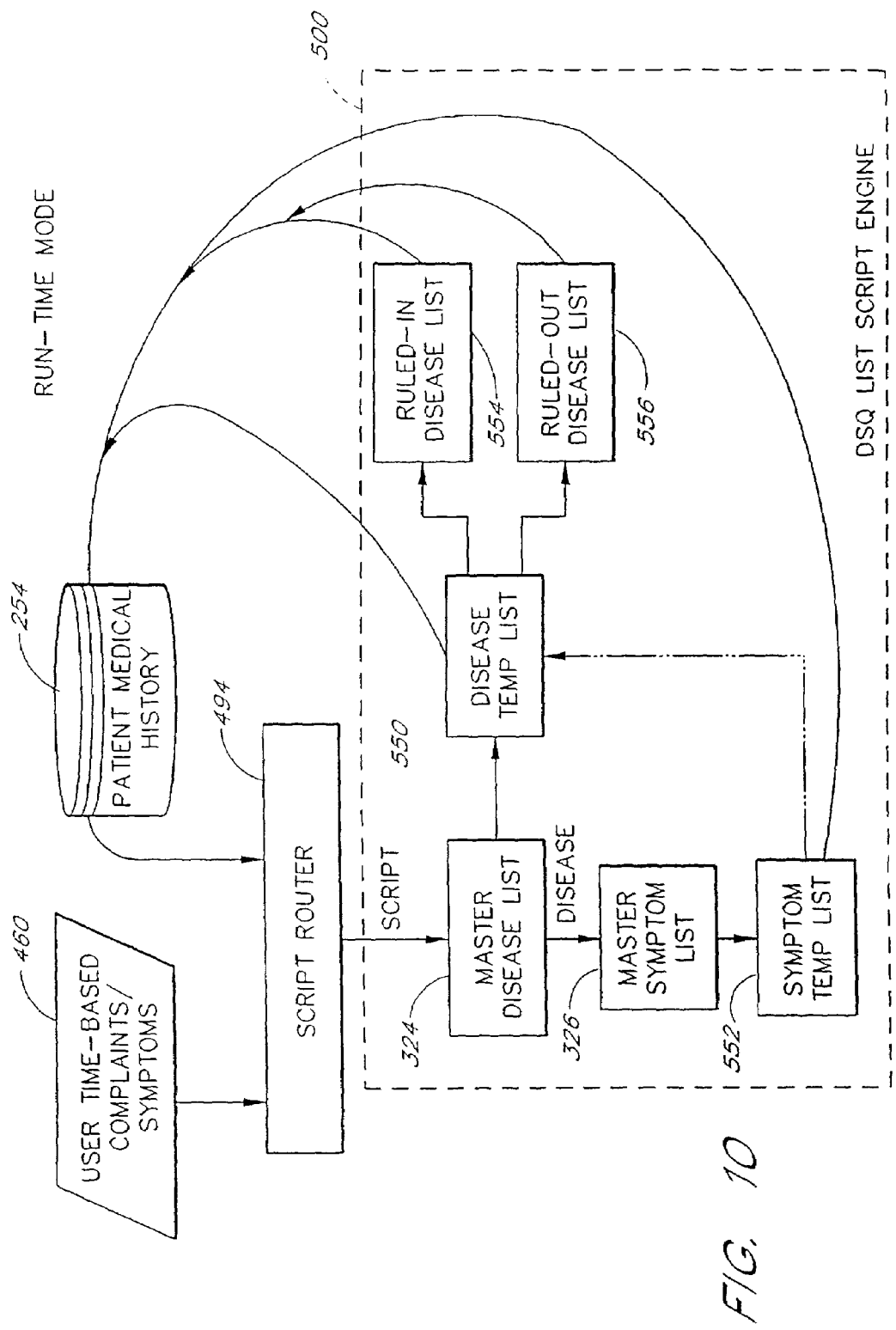

Referring to FIG. 9, the DSQ script engine process 500 will now be described. Beginning at a start state 530, the process 500 proceeds to state 532 to access the selected DSQ list file passed to it by the diagnostic script engine. Proceeding to state 534, process 500 initializes the temp lists utilized by the script engine. Referring temporarily to FIG. 10, process 500 initializes the symptom temp list 552 to be cleared and initializes the disease temp list 550 to have all of the diseases of the master disease list 324. At this point, process 500 selects one of the diseases to be processed and then selects a symptom to be asserted in the disease. To determine the presence or absence of the symptom in the patient, process 500 continues at state 536 to select the first question of the symptom to be asked of the patient. At state 538, process 500 asks the question of the patient. Moving to state 540, process 500 receives the patient's response and checks for correctness of their response according to the asked question. The patient's response is used then to update the DSQ temp lists at state 542.

Proceeding to a decision state 544, process 500 determines if a diagnosis or a terminus of the script has been reached. If it has not, process 500 proceeds to state 546 to select either the next question in the current symptom, or, if all the questions for the current symptom have been asked, to proceed to the next symptom for the current disease. If all the questions in the current disease have been asked, process 500 moves to the next disease and asks the questions necessary for that disease. Process 500 loops at states 538 through 546 until the end of the script is reached, a diagnosis is achieved, the user requests the script to be adjourned, or the script engine determines that the script should be terminated. When the diagnosis or terminus has been reached, process 500 either returns the diagnosis at state 541, refers the patient to a different script at state 543, adjourns the current script at state 545, or terminates the current script at state 547. Process 500 completes at a return state 548.

Referring now to FIG. 10, a portion of the lists utilized during run-time operation of the DSQ list script engine 500 will be described. Based on user input 460 and the time since the symptoms have begun, the script router 494 (FIG. 8*a*) of the diagnostic script engine 490 identifies a script to be passed to the DSQ list script engine 500. The records of the current patient from the patient medical history 254 are also used by the script router 494. Using the medical diagnostic script received from the script router, the DSQ list script engine 500 accesses the master disease list 324. The diseases in the master disease list are copied to a disease temp list 550. At the appropriate time during operation of the DSQ list script engine 500, symptoms from the master symptom list 326 of the current disease are selectively copied to the symptom temp list 552, as will be described in conjunction with FIG. 12. As symptoms are asserted during the patient interview, symptom weights and/or question weights for the symptoms will be added to the score for the current disease in the disease temp list 550. When a score for a particular disease reaches a ruled-in threshold, the disease is moved to the ruled-in disease list 554. Alternatively, if the score for the current disease reaches the ruled-out disease threshold, the disease is moved to the ruled-out disease list 556. Asserted symptoms, ruled-in diseases, ruled-out diseases, and diseases neither ruled-in nor ruled-out may all be stored in the patient medical history 254. At the completion of a script or at a terminus or checkpoint during the script, diseases left in the disease temp list 550 may also be written to the patient medical history 254. Alternatively, the patient symptom and disease information may be written to the local user data storage 184 (FIG. 6*b*) instead of the central patient medical history 254.

Figure 11:
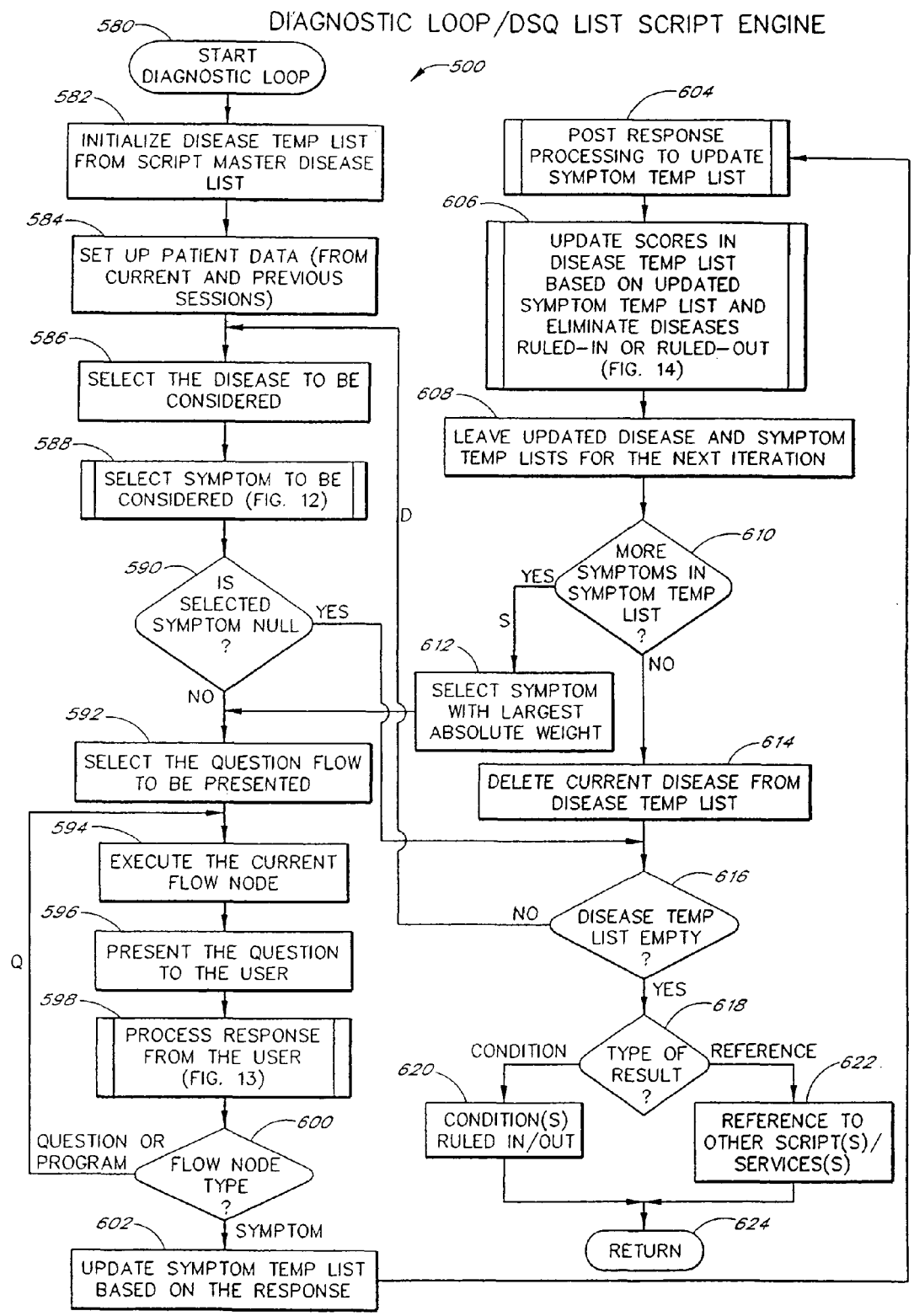

Referring now to FIG. 11, the operation of the DSQ list script engine 500 will be described. This description will provide more detail than the overview of the script engine process provided in conjunction with FIG. 9. Beginning at a start state 580, the script engine process 500 proceeds to state 582, wherein the disease temp list 550 is initialized from the script master disease list 324 (FIG. 10). Moving to state 584, the script engine process accesses patient data from current and/or previous patient sessions. The script engine process 500 utilizes the MDATA support system 440 (FIG. 6*a*) and the databases 442 to get the patient data and any other data necessary. Alternatively, the patient data may be retrieved from the local user data storage 184 (FIG. 6*b*).

Advancing to state 586, the script engine process 500 selects the disease to be considered. Various methods may be utilized in selecting the order of the diseases to be considered. For example, the most urgent diseases may be considered first, followed by the serious diseases and then the common diseases. Alternatively, or in conjunction with the urgent/serious model, the first diseases to be considered may be the most prevalent in the population that the patient is in. The script engine process may utilize the telephone number, postal zip code, or other sources of location information from the patient's history to identify the population group or location that the patient is in. An alternative for selecting the disease order once the process has started is to use the disease with the highest total of symptom weights, i.e., the disease which is nearest to being diagnosed. Preferably, the script coordinator arranges the diseases for the current script in the order they are to be considered. After the current disease to be considered is determined, the script engine process 500 proceeds to the "select symptom to be considered" process 588. Process 588 determines the symptoms to be considered for the current disease and will be further described in conjunction with FIG. 12.

Script engine process 500 checks to see if a selected symptom null flag, which may be set during process 588, is asserted at decision state 590. If the selected symptom flag is null for the current disease, process 500 advances to a decision state 616 to determine if there are more diseases to consider. However, if the selected symptom flag is not null, script engine process 500 proceeds to state 592 to select the question flow to be presented to the patient. Associated with each symptom is a question logic flow that can elicit the symptom. A logic flow can be thought of as a "complex question," i.e., a question that consists of several questions and can produce one of several answers. Preferably, the question flow which contains, i.e., can generate as a response, the symptom which currently has the highest chance of ruling in the disease under consideration should be selected. Advancing to state 594, script engine process 500 then executes the current flow node. Proceeding to state 596, script engine process 500 presents the question part of the flow node to the user. Every question preferably consists of a set of information text, instruction text, and a question. To present the question, the script first outputs the information text to the patient, then the instruction text, and finally the question text. The question text indicates to the patient that a response is expected at the present time.

Continuing at a handle response process 598, the script engine processes the response from the user. Process 598 will be further described in conjunction with FIG. 13. The flow node preferably is one of three types: symptom, question, or program. Script engine process 500 determines the flow node type at a decision state 600. If the node type is question or program, script engine process 500 moves to state 594 (question loop Q) to execute the next flow node. However, if the flow node type is of the symptom type, process 500 proceeds to state 602 to update the symptom temp list 552 (FIG. 10), based on the received response from the patient. Based on the response, a weight is assigned for the current symptom. Alternatively, if the current symptom utilizes multiple questions, some of which have associated weights, the weight (if present) for the current question is accumulated for the current symptom.

When the DSQ script has obtained a symptom, it updates all diseases that have the symptom. That is, a single answer from the patient can change the symptom weighing of all diseases being considered. This "promotes" one or more diseases to being closer to the diagnostic thresholds.

Proceeding to a function 604, the script engine process 500 performs post-response processing to further update the symptom temp list 552. Examples of post-response processing include if-then relationships, simultaneous relationships, sequencing relationships and other similar types of relationships. For example, if a symptom severity value is 9, then a weight of 75 might be added to the diagnosis of biliary colic, and a weight of 50 might be subtracted from the diagnosis of appendicitis. Other post-response relationships were previously discussed in conjunction with FIG. 4b (capture disease knowledge). After the post-response processing has been completed, the script engine process 500 proceeds to the update disease lists process 606. At process 606, the script engine updates the scores in the disease temp lists based on the updated symptom temp list 552 and eliminates ruled-in or ruled-out diseases. The update disease list process 606 will be further described in conjunction with FIG. 14.

At the completion of process 606, some diseases may be ruled in or ruled out, thereby reducing the length of the disease temp list 550 (FIG. 10). However, if either the ruled-in threshold or the ruled-out threshold has not been reached, the disease is not removed from the disease temp list. Thus, at state 608, an updated disease temp list and an updated symptom temp list are left for the next iteration of checking symptoms for diseases. Moving to a decision state 610, the script engine process 500 determines if there are more symptoms in the symptom temp list 552 for the current disease. If so, the script engine process 500 selects the symptom with the largest weight, based on absolute value, associated with it at state 612 and then proceeds to state 592 (symptom loop S) to select the question flow for that new symptom. However, if there are no additional symptoms in the symptom temp list 552, as determined at decision state 610, the script engine process 500 proceeds to state 614 to delete the current disease from the disease temp list 550.

Proceeding to the decision state 616, the script engine process 500 determines if the disease temp list 550 for the current script is empty. If it is not, the script engine process 500 moves to state 586 (disease loop D) to consider the next disease in the script. If the disease temp list 550 for the current script is empty, the script engine process 500 proceeds to a decision state 618 to determine the type of result of the script. At state 620, one of the possible results is that one or more diseases have been ruled in or have been ruled out. At state 622, another type of result is that the script engine has determined to reference another script or another service. The script engine process 500 completes at a return state 624 and returns to the diagnostic process 490 (FIG. 8a).

Figure 12:
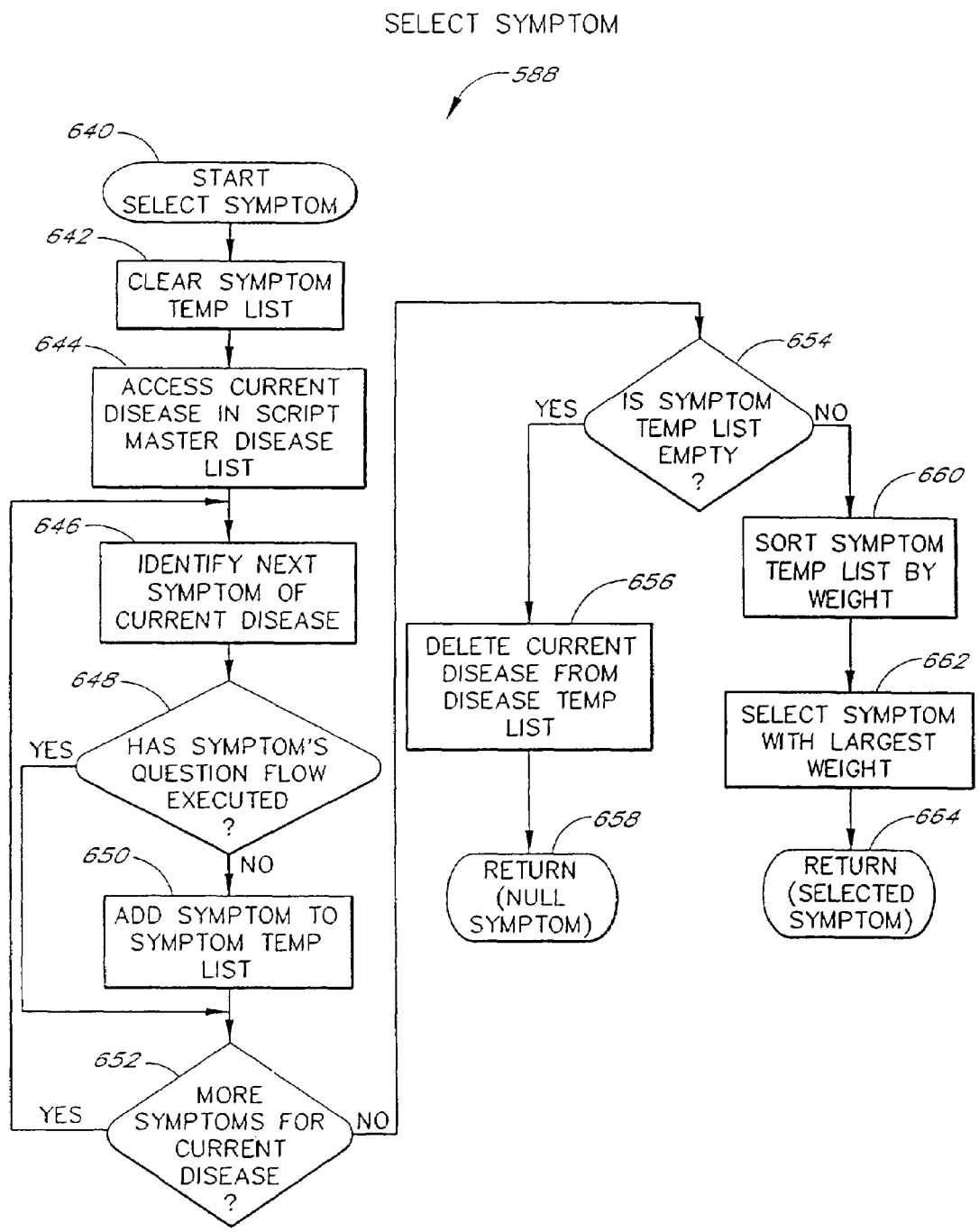
FIG. 12 is a flow diagram of the "select symptom" (select symptom to be considered) process identified in FIG. 11.

Referring to FIG. 12, the select symptom process 588, referenced in FIG. 11, will now be described. Beginning at a start state 640, the select symptom process 588 proceeds to state 642 to clear the symptom temp list 552 (FIG. 10). Proceeding to state 644, the select symptom process 588 accesses the current disease in the script master disease list 324 (FIG. 10). Advancing to state 646, process 588 identifies the next symptom of the current disease. Continuing at a decision state 648, process 588 determines if the symptom's question flow has previously been executed for this patient. For example, the symptom may have been determined in another disease or even in another script for this patient. If the question flow has not been previously executed, process 588 proceeds to state 650 and adds the symptom to the symptom temp list. After adding the symptom to the symptom temp list, or if the symptom's question flow has been previously executed, process 588 moves to a decision state 652. At decision state 652, process 588 determines if there are more symptoms for the current disease. If so, process 588 moves back to state 646 to identify the next symptom of the current disease.

If there are no more symptoms for the current disease, as determined at state 652, process 588 continues at a decision state 654 to determine if the symptom temp list 552 is empty. If it is, select symptom process 588 moves to state 656 to delete the current disease from the disease temp list 550. This would happen, for example, if all the symptoms for the disease had been previously considered at an earlier time in this or another script. In this situation, the select symptom process 588 returns at state 658 will a null symptom flag. Returning to decision state 654, if the select symptom process 588 determines that the symptom temp list is not empty, execution continues at state 660 wherein the symptom temp list is sorted by the absolute value of the weight. Proceeding to state 662, process 588 selects the symptom with the largest absolute value of the weight. The select symptom process 588 returns at state 664 to process 500 (FIG. 11) with the selected symptom.

Figure 13:
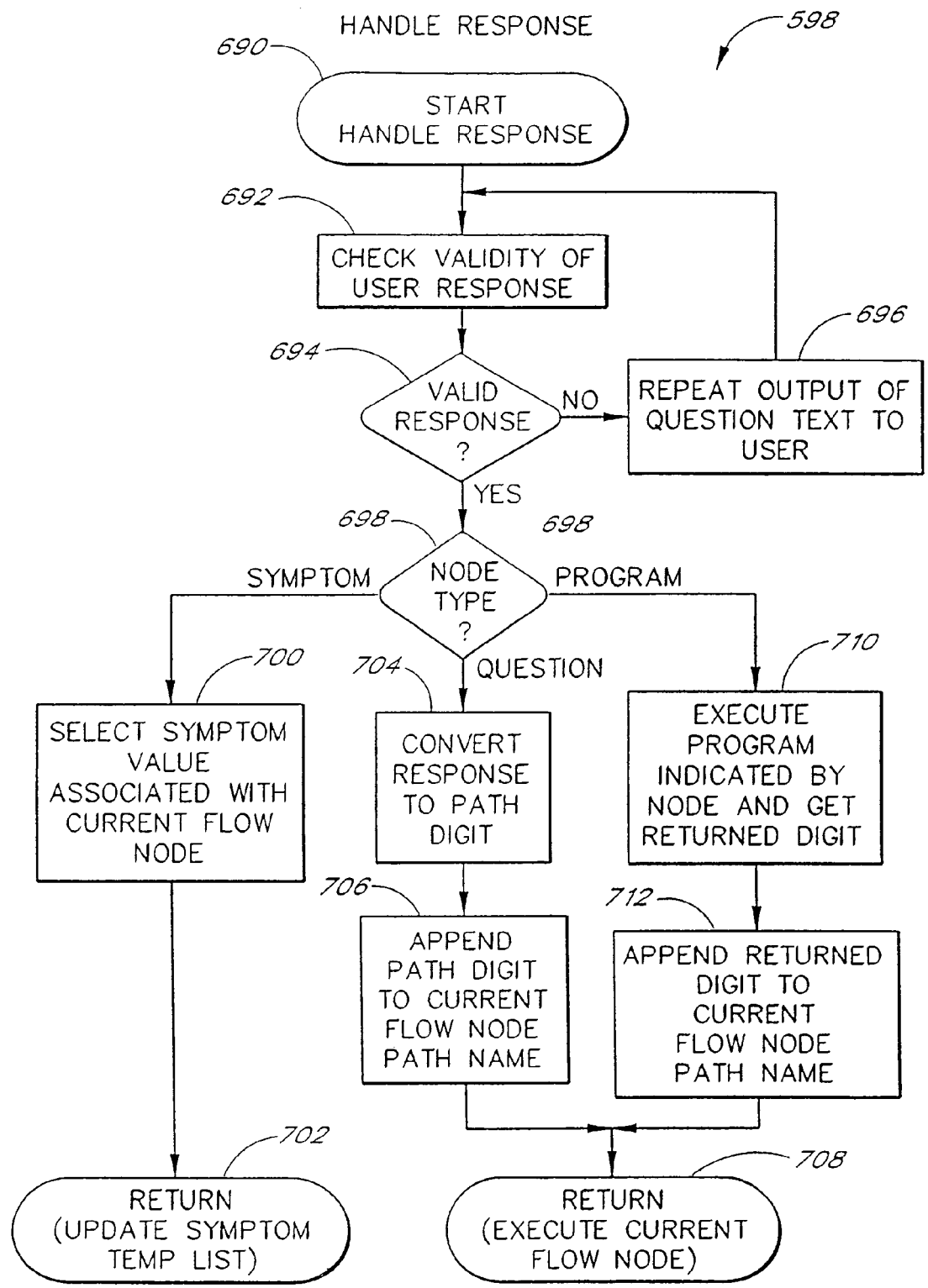
FIG. 13 is a flow diagram of the "handle response" (process response from the user) process identified in FIG. 11.

Referring to FIG. 13, the handle response process 598, referenced in FIG. 11, will now be described. Beginning at a start state 690, process 598 proceeds to state 692 to check the validity of a user response. Proceeding to a decision state 694, process 598 determines if the response is valid. If the response is not valid, process 598 proceeds to state 696 to repeat the output of the question text to the user and then moves back to state 692 to check the validity of the user response. A check for a time-out situation occurs during the handle response process 598. The time-out is evaluated to see if it could mean a possible loss of consciousness or a change in mental status. If so, a mental status subroutine could be invoked or emergency medical personnel may be called, for example.

If the response is determined to be valid at the decision state 694, process 598 proceeds to a decision state 698 to determine the type of node currently being processed by the DSQ script engine 500. If the node type is a symptom node, process 598 proceeds to state 700 to select the symptom value associated with the current flow node. A symptom node returns the symptom as the answer to the complex question. The symptom value is then returned at state 702 to the symptom script engine process 500 (FIG. 11). If the node type is a question node, process 598 proceeds to state 704 to convert the response to a path digit. Advancing to state 706, process 598 appends the path digit to the current flow node path name. State 704 and 706 are used to identify the next question node to be executed. Returning to decision state 698, if the node type is determined to be a program node, process 598 proceeds to state 710. At state 710, process 598 executes the program indicated by the current node and gets a return digit. Continuing at state 712, process 598 appends the return digit to the current flow node path name. State 710 and 712 are used to identify the next question node to be executed. The program executed at state 710 may be a sub-script or other function or subroutine needed to elicit additional medical information from the patient. At the completion of either state 706 or 712, process 598 returns at return state 708 to the DSQ script engine process 500 (FIG. 11).

Figure 14:
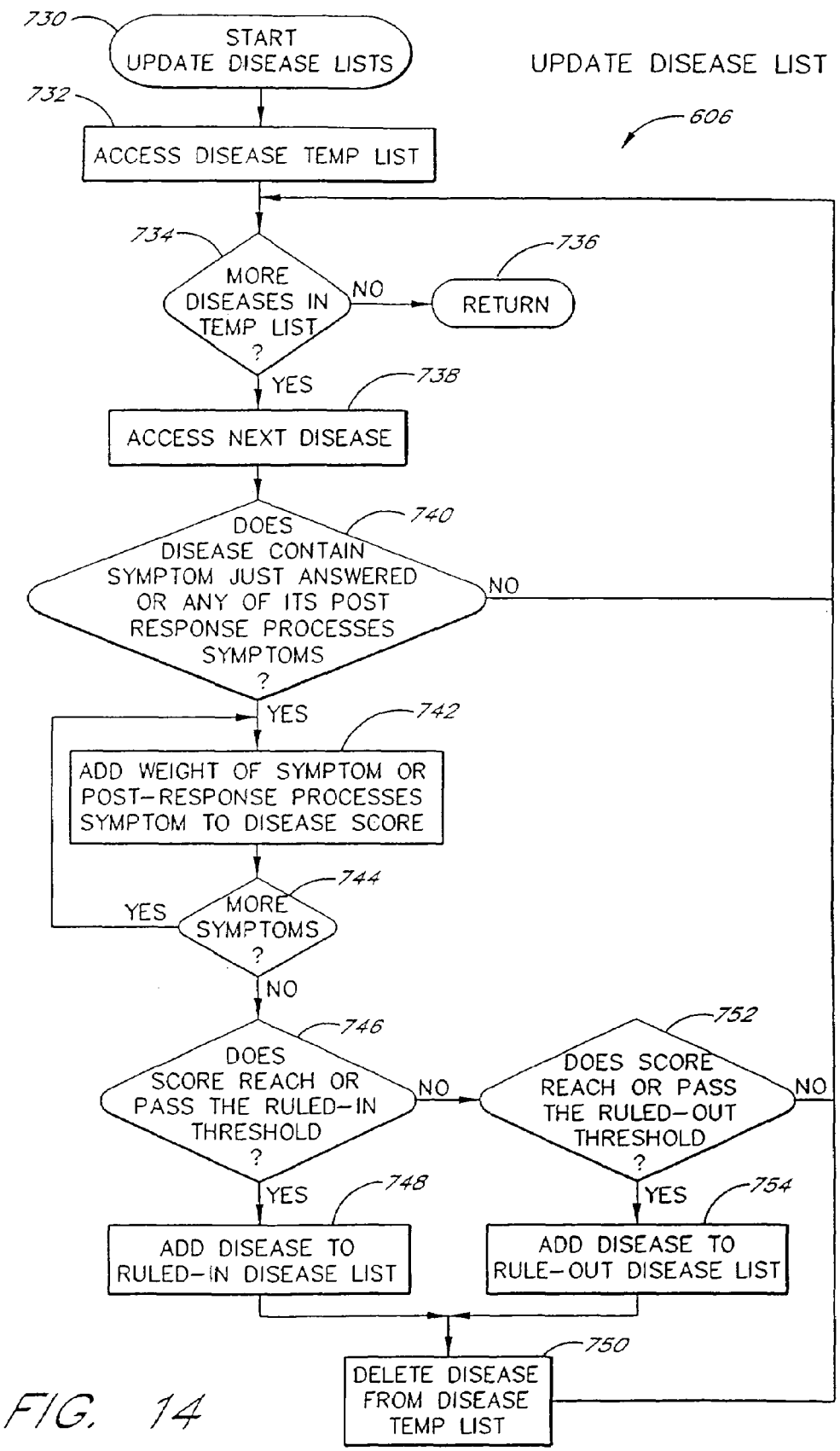
FIG. 14 is a flow diagram of the "update disease lists" (update scores in disease temp list based on updated symptom list and eliminate diseases ruled-in or ruled-out) process identified in FIG. 11.

Referring to FIG. 14, the update disease lists process 606, referred to in FIG. 11, will now be described. Beginning at a start state 730, process 606 proceeds to state 732 to access the disease temp list 550 (FIG. 10). Continuing at a decision state 734, process 606 determines if there are more diseases in the disease temp list 550. If not, process 606 returns at a return state 736 to the DSQ script engine process 500 (FIG. 11). However, if there are more diseases in the temp list, process 606 proceeds to state 738 to access the next disease in the disease temp list 550. Proceeding to a decision state 740, process 606 determines if the current disease contains the symptom just answered by the patient or any of its post-response processed symptoms, such as determined at function 604 (FIG. 11). If so, process 606 moves to state 742 and adds the weight of the symptom just answered or the post-response process symptom to the score of the current disease. Proceeding to a decision state 744, process 606 determines if there are additional symptoms having weights that need to be added to the current disease score. This typically would happen if there are multiple post-response process symptoms. If so, process 606 moves back to state 742 to add the weight of these additional symptoms to the disease score. If there are no more symptoms that need to be processed, as determined at state 744, process 606 proceeds to a decision state 746.

At decision state 746, process 606 determines if the disease score has reached or passed the ruled-in threshold. The ruled-in threshold preferably has a value of 1,000, but other ruled-in threshold scores could be utilized. If so, process 606 proceeds to state 748 to add the current disease to the ruled-in disease list 554 (FIG. 10). Moving to state 750, process 606 deletes the current disease from the disease temp list 550 (FIG. 10) and then moves back to decision state 734 to determine if there are more diseases in the temp list 550.

Returning to decision state 746, if the score has been determined to not reach or pass the ruled-in threshold, process 606 proceeds to a decision state 752. At decision state 752, process 606 determines if the disease score has passed or has reached the ruled-out threshold. If so, process 606 moves to state 754 to add the current disease to the ruled-out disease list 556 (FIG. 10). Advancing to state 750, process 606 deletes the disease from the disease temp list 550 and moves back to decision state 734 to check for additional diseases in the disease temp list 550.

Returning to decision state 752, if the disease score is not less than or equal to the ruled-out threshold, process 606 moves back to decision state 734 to check for additional diseases in the temp list 550. Returning to decision state 740, if the current disease does not contain the symptom just answered or any of its post-response processed symptoms, process 606 moves back to decision state 734 to check for additional diseases in the temp list 550.

The use of the ruled-in threshold and the ruled out threshold has certain implications as follows:
- the weight of a symptom can be given as a positive or negative number;
- two running scores are kept for each disease: one positive and one negative;
- positive weights are added to the positive score and negative weights to the negative score;
- weights are not subtracted;
- two threshold are used, a positive one (e.g. 1000 or 10000) to rule diseases in and a negative one (e.g. −1000 or −10000 to rule diseases out;
- when the positive score reaches or exceeds the positive threshold, the disease is ruled-in;
- when the negative score reaches or exceeds the negative threshold, the disease is ruled-out;
- if a disease reaches neither threshold by the end of the script, it is left in an "undecided" list of diseases, which can be stored in the patient medical history.

Figure 15:
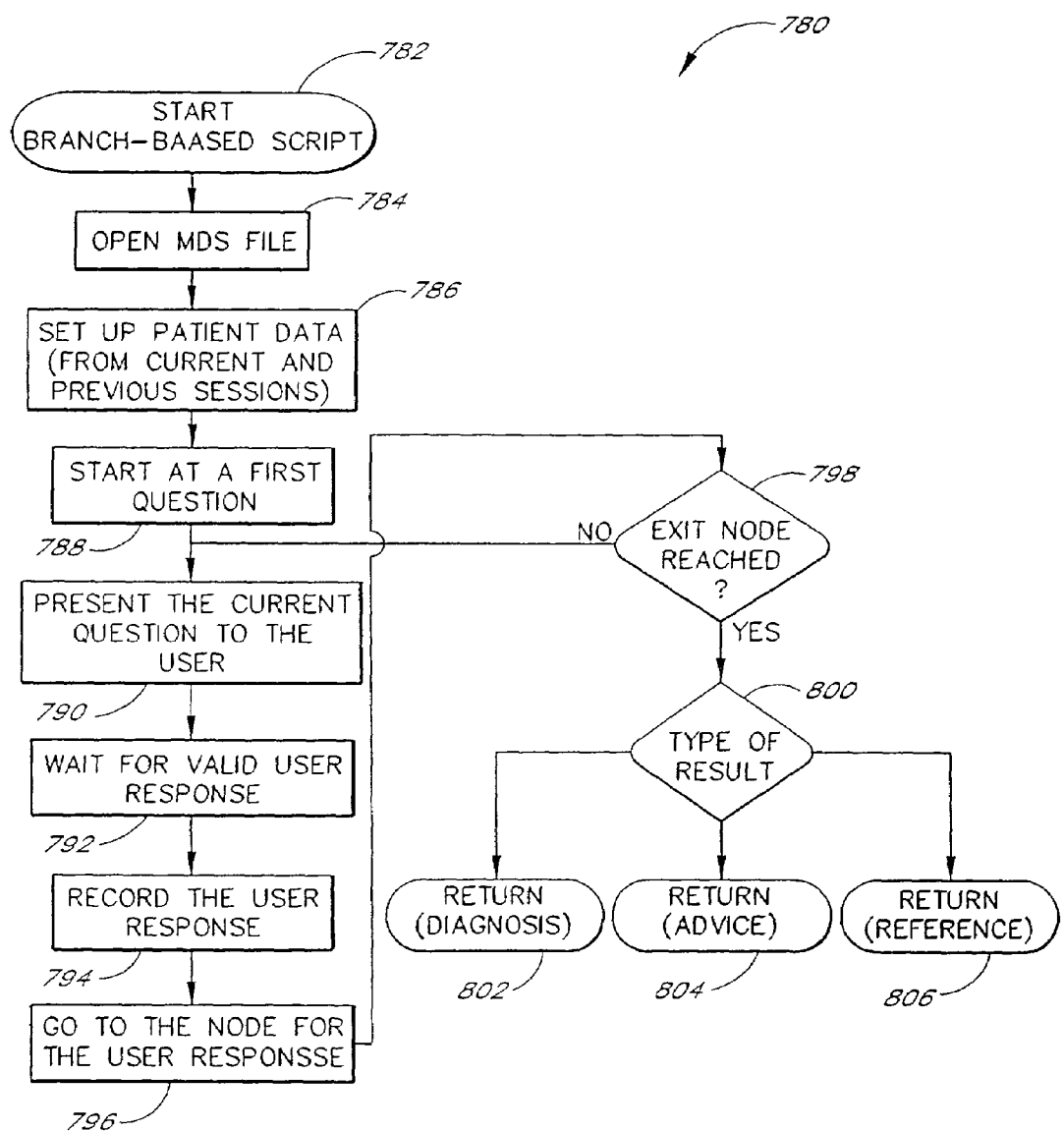

Referring to FIG. 15, an alternative embodiment for generating medical advice or a diagnosis using branch-based scripts will now be described. Beginning at a start state 782, the branch-based script process 780 proceeds to state 784 to open a branch-based medical diagnostic script file. Proceeding to state 786, process 780 sets up the patient data from either current and/or previous sessions with the patient. Script process 780 proceeds to state 788 and starts at a first question in the script. Advancing to state 790, script process 780 presents the current question to the user. Continuing at state 792, script process 780 waits for a valid user response. Moving to state 794, script process 780 records the user response. At state 796, script process 780 goes to the node corresponding with the user response. Continuing at a decision state 798, script process 780 determines if the next node is an exit node. If not, process 780 continues at state 790 and presents the next question to the user. The script process 780 loops on states 790 through 798 according to the sequence of the predetermined script nodes until an exit node is reached. When the exit node is reached, script process 780 moves to a decision state 800 to determine the type of result of the script. The branch-based script 780 may return a diagnosis at a return state 802, advice at a return state 804, or a reference to another script at a return state 806.

VI. Advantages of List-Based Processing

The List-Based Processing system provides advantages of speed, precision and completeness over other methods of medical diagnoses. Specifically, the List-Based Processing approach:
- organizes medical knowledge into lists that others can process;
- presents diagnosis in a way that can be checked for correctness and completeness;
- generates better scripts than humans can write using branch-based scripts;
- simplifies updating scripts as medical knowledge changes;
- allows testing by automated means;
- can be used as a callable function from branch-based scripts;
- is computer platform-, medium-, and language-independent;
- allows scripts to be more easily translated into other human languages;
- reflects the way doctors actually diagnose.

Specific blocks, sections, devices, functions and modules may have been set forth. However, a skilled technologist will realize that there are many ways to partition the system of the present invention, and that there are many parts, components, modules or functions that may be substituted for those listed above.

While the above detailed description has shown, described, and pointed out the fundamental novel features of the invention as applied to various embodiments, it will be understood that various omissions and substitutions and changes in the form and details of the system illustrated may be made by those skilled in the art, without departing from the intent of the invention.

APPENDIX

Exemplary DSQ List-Based Script

This listing shows a more extensive sample of an ASCII file that containslists used as the starting point for List-Based Processing. The list is intended only to show formats and relationships. It may not convey correct or complete medical information. The chief complaint for this exemplary script is "malaise".

MALARIA.TXT
DEF H
  h_format 5
  h_complaint s_malaise
END H
DEF D
d_falc "084.0" "Falciparum Malaria"
  s_tropics 200
  s_lethargic 100
  s_fever 200
  s_chills 200
  s_nochills −100
  s_sweats 200
  s_nosweats −100
  s_cfsinorder 200
  s_cfsnotinorder 100
  s__2bouts_other 250
  s__3bouts_other 250
  s_pnotest 5
  s_pnegative −700
  s_pfalcip 700
  s_pvivax −700
  s_povale −700
  s_pmalar −700
  s_pmixed −700
d_vivax "084.1" "Vivax Malaria"
  s_tropics 200
  s_lethargic 100
  s_fever 200
  s_chills 200
  s_nochills −100
  s_sweats 200
  s_nosweats −100
  s_cfsinorder 200
  s_cfsnotinorder100
  s__2bouts__48 350
  s__3bouts__48 450
  s_pnotest 5
  s_pnegative −700
  s_pfalcip −700
  s_pvivax 700
  s_povale −700
  s_pmalar −700
  s_pmixed −700
d_quartan "084.2" "Quartan Malaria"
  s_tropics 200
  s_lethargic 100
  s_fever 200
  s_chills 200
  s_nochills −100
  s_sweats 200
  s_nosweats −100
  s_cfsinorder 200
  s_cfsnotinorder 100
  s__2bouts__72 350
  s__3bouts__72 450
  s_pnotest 5
  s_pnegative −700
  s_pfalcip −700
  s_pvivax −700
  s_povale −700
  s_pmalar 700
  s_pmixed −700
d_ovale "084.3" "Ovale Malaria"
  s_tropics 200
  s_lethargic 100
  s_fever 200
  s_chills 200
  s_nochills −100
  s_sweats 200
  s_nosweats −100
  s_cfsinorder 200
  s_cfsnotinorder 100
  s__2bouts_other 250
  s__3bouts_other 350
  s_pnotest 5
  s_pnegative −700
  s_pfalcip −700
  s_pvivax −700
  s_povale 700

```
    s_pmalar −700
    s_pmixed −700
d_mixed "084.5" "Mixed Malaria"
    s_tropics 200
    s_lethargic 100
    s_fever 200
    s_chills 200
    s_nochills −100
    s_sweats 200
    s_nosweats −100
    s_cfsinorder 200
    s_cfsnotinorder 100
    s__1bout__23days 200
    s__1bout_other 200
    s__2bouts_other 200
    s__3bouts_other 300
    s_pnotest 5
    s_pnegative −700
    s_pfalcip −700
    s_pvivax −700
    s_povale −700
    s_pmalar −700
    s_pmixed 700
d_unspec "084.6" "Malaria, unspec"
    s_tropics 200
    s_lethargic 100
    s_fever 200
    s_chills 200
    s_nochills −100
    s_sweats 200
    s_nosweats 100
    s_cfsinorder 200
    s_cfsnotinorder 100
    s_pnotest 100
d_notmal "-" "Not Malaria"
    s_nofever 100
    s_nochills 300
    s_nosweats 300
    s_nocfs 700
    s_cfsnotinorder 300
    s_pnegative 1000
    s_pfalcip −600
    s_pvivax −600
    s_povale −600
    s_pmalar −600
    s_pmixed −600
END D
DEF S
    s_malaise 0 "general ill feeling"
    s_tropics f_tropics "recently in tropics"
    s_nottropics f_tropics "not recently in tropics"
    s_lethargic f_lethargic "has been tired/lethargic"
    s_notlethargic f_lethargic "not tired/lethargic"
    s_fever f_fever "has fever"
    s_nofever f_fever "has no fever"
    s_chills f_chills "has chills"
    s_nochills f_chills "has no chills"
    s_sweats f_sweats "has sweating"
    s_nosweats f_sweats "has no sweating"
    s_nocfs f_cfs "did not have CFS"
    s_cfsinorder f_cfs "had CFS"
    s_cfsnotinorder f_cfs "had CFS, but not in order"
    s_pnotest f_ptest "not tested for Plasmodia"
    s_pnegative f_ptest "plasm test negative"
    s_pfalcip f_ptest "test+ for *P. falciparum*"
    s_pvivax f_ptest "test+ for *P. vivax*"
    s_povale f_ptest "test+ for *P. ovale*"
    s_pmalar f_ptest "test+ for *P. malariae*"
    s_pmixed f_ptest "test+ for mixed Plasmodia"
    s__1bout__1day f_cfs "1 CFS bout lasting 1 day"
    s__1bout__23days f_cfs "1 CFS bout lasting 2-3 days"
    s__1bout_other f_cfs "1 cfs bout of unk duration"
    s__2bouts__48 f_cfs "2 CFS bouts, 48 h apart"
    s__2bouts__72 f_cfs "2 CFS bouts, 72 h apart"
    s__2bouts_other f_cfs "2 CFS bouts; unknown interval"
    s__3bouts__48 f_cfs "3+ CFS bouts every 48 hours"
    s__3bouts__72 f_cfs "3+ CFS bouts every 72 hours"
    s__3bouts_other f_cfs "3+ CFS bouts of unk interval"
END S
DEF I
    s_nochills s_nocfs
    s_nofever s_nocfs
    s_nosweats s_nocfs
    s_chills s_fever s_sweats s_cfs
END I
DEF F
f_tropics
    "1" q_tropics
    "11" s_tropics
    "12" s_nottropics
f_lethargic
    "1" q_lethargic
    "11" s_lethargic
    "12" s_notlethargic
f_fever
    "1" q_fever
    "11" s_fever
    "12" s_nofever
f_chills
    "1" q_chills
    "11" s_chills
    "12" s_nochills
f_sweats
    "1" q_sweats
    "11" s_sweats
    "12" s_nosweats
f_cfs
    "1" q_cfs
    "12" s_nocfs
    "11" q_cfsorder
    "112" 5_cfsnotinorder
    "111" q_cfsbouts
    "1110" s_nocfs
    "1111" q_d1bout
    "11111" s__1bout1day
    "11112" s__1bout__23days
    "11113" s__1bout_other
    "1112" q_d2bouts
    "11121" s__2bouts__48
    "11122" s__2bouts__72
    "11123" s__2bouts_other
    "1113" q_d3bouts
    "11131" s__3bouts__48
    "11132" s__3bouts__72
    "11133" s__3bouts_other
f_ptest
    "1" q_test
    "12" s_pnotest
    "11" q_pfound
    "110" s_pnegative
    "111" s_pfalcip
    "112" s_pvivax
    "113" s_povale
    "114" s_pmalar
```

"115" s_pmixed
END F
DEF Q
    q_tropics 0 t_qtropics 12 t_kyes t_kno
    q_lethargic 0 t_qlethargic 12 t_kyes t_kno
    q_fever 0 t_qfever 12 t_kyes t_kno
    q_chills 0 t_qchills 12 t_kyes t_kno
    q_sweats 0 t_qsweats 12 t_kyes t_kno
    q_cfs 0 t_qcfs 12 t_kyes t_kno
    q_cfsorder 0 t_qcfsorder 12 t_kyes t_kno
    q_ptest 0 t_qptest 12 t_kyes t_kno
    q_pfound 0 t_qpfound 012345 t_knone t_falc t_viv t_ov t_mal t_mix
    q_cfsbouts 0 t_qcfsbouts 0123 t_knone t_kane t_ktwo t_k3plus
    q_d1bout 0 t_qd1bout 123 t_kup1day t_k23days t_kother
    q_d2bouts 0 t_qd2bouts 123 t_k48hours t_k72hours t_kother
    q_d3bouts 0 t_qd3bouts 123 t_k48hours t_k72hours t_kother
END Q
DEF T
    t_falc FALCIPARUM
    t_mal MALARIAE
    t_mix MIXED
    t_ov OVALE
    t_viv VIVAX
    t_k23days 2-3 DAYS
    t_k3plus THREE+
    t_k48hours 48 HOURS
    t_k72hours 72 HOURS
    t_kno NO
    t_knone NONE
    t_kone ONE
    t_kother OTHER
    t_ktwo TWO
    t_kup1day UP TO ONE DAY
    t_kyes YES
    t_qcfs Did you have Chills, Fever, and Sweating?
    t_qcfsbouts How many bouts of C-F-S did you have?
    t_qcfsorder Did you have C-F-S in that order?
    t_qchills Do you have chills?
    t_qd1bout How long did that 1 bout last?
    t_qd2bouts What was the time between those 2 bouts?
    t_qd3bouts How far apart were these bouts?
    t_qfever Do you have fever?
    t_qlethargic Have you been tired or lethargic?
    t_qpfound What Plasmodia were found in blood?
    t_qptest Did you have a blood test for Plasmodia?
    t_qsweats Do you have sweating?
    t_qtropics Have you been in the tropics recently?
END T

What is claimed is:

1. A computerized medical diagnostic system, comprising:
    a storage having a list of diseases, each disease associated with a list of symptoms, and each symptom associated with a list of questions; and
    a storage having a script engine operating on a computer and configured to:
        repetitively ask questions selected from the lists of questions to elicit responses, the responses establishing symptoms selected from the lists of symptoms, each established symptom contributing a weight to an accumulated total weight for a disease selected from the lists of diseases, and
        determine whether the accumulated total weight for the selected disease reaches or passes a threshold so as to declare a diagnosis.

2. The system defined in claim 1, wherein the symptom is established based on a presence or absence of one or more other symptoms.

3. The system defined in claim 1, wherein a presence of a selected set of symptoms adds additional weight to the accumulated total weight of at least one of the diseases.

4. The system defined in claim 1, wherein a symptom at a first selected time during operation of the diagnostic system is weighted differently than the symptom at a second selected time.

5. The system defined in claim 1, wherein the weight of a symptom established at a first severity is different than the weight of the symptom established at a second severity.

6. The system defined in claim 1, wherein a selected set of symptoms that occur in a specified sequence over time lends a different accumulated weight to the total weight than an accumulation of the individual weights of the selected set of symptoms that do not occur in the specified sequence.

7. The system defined in claim 1, wherein a sequence of an onset or ending of a selected set of symptoms lends a different accumulated weight to the total weight than an accumulation of individual weights of the selected symptoms alone.

8. The system defined in claim 1, wherein the disease is ruled-in for further diagnostic inquiry based on the accumulated total weight.

9. The system defined in claim 8, wherein a degree of certainty of ruling-in the disease is provided.

10. The system defined in claim 1, wherein the disease is ruled-out for further diagnostic inquiry based on the accumulated total weight.

11. The system defined in claim 10, wherein a degree of certainty of ruling-out the disease is provided.

12. The system defined in claim 1, wherein questions for diseases deemed urgent are asked before questions for non-urgent diseases.

13. The system defined in claim 1, wherein the script engine is further configured to determine whether the accumulated total weight for a disease reaches or passes a rule-out threshold so as to eliminate a possible diagnosis.

14. The system defined in claim 1, wherein a plurality of diagnoses, each diagnosis having a degree of certainty, are accumulated into a patient specific differential diagnosis list.

15. The system defined in claim 1, wherein the script engine is configured to repetitively ask questions selected from two or more lists of questions to elicit responses from a patient.

16. The system defined in claim 1, wherein at least a portion of the symptoms in the lists of symptoms are associated with a plurality of questions to be asked, and wherein weights are assigned to possible responses of the plurality of questions.

17. The system defined in claim 16, wherein after the plurality of questions are answered, a symptom score is totaled of the weights corresponding to the responses.

18. The system defined in claim 17, wherein the symptom score is compared to a threshold for the symptom, and the symptom is established if the symptom score reaches or passes the symptom threshold.

19. The system defined in claim 18, wherein the weight of the established symptom is associated with the symptom score.

20. The system defined in claim 16, wherein at least some of the weights assigned to the possible responses of the plurality of questions have different values.

21. The system defined in claim 1, wherein the weight contributed by an established symptom is a negative integer.

22. The system defined in claim 1, wherein the storage having the list of diseases and the storage having the script engine are the same device.

23. A computerized medical diagnostic method, comprising:
providing a list of diseases, each disease associated with a list of symptoms, and each symptom associated with a list of questions; and
executing a script engine on a computer comprising:
repetitively asking questions selected from the lists of questions to elicit responses;
establishing symptoms selected from the lists of symptoms based on the responses;
contributing a weight to an accumulated total weight for a disease selected from the lists of disease based on each established symptom; and
determining whether the accumulated total weight for the selected disease reaches or passes a threshold so as to declare a diagnosis.

24. The method defined in claim 23, wherein establishing symptoms is based on a presence or absence of one or more other symptoms.

25. The method defined in claim 23, additionally comprising adding additional weight to the accumulated total weight of at least one of the diseases based on a presence of a selected set of symptoms.

26. The method defined in claim 23, wherein contributing a weight comprises weighting a symptom at a first selected time during execution of the script engine differently than the symptom at a second selected time.

27. The method defined in claim 23, wherein contributing a weight comprises weighting a symptom established at a first severity differently than the weight of the symptom established at a second severity.

28. The method defined in claim 23, additionally comprising contributing an accumulated weight to the total weight for a selected set of symptoms that occur in a specified sequence over time that is different than an accumulation of the individual weights of the selected set of symptoms that do not occur in the specified sequence.

29. The method defined in claim 23, additionally comprising contributing an accumulated weight to the total weight for a sequence of an onset or ending of a selected set of symptoms that is different than an accumulation of individual weights of the selected symptoms alone.

30. The method defined in claim 23, additionally comprising ruling-in the disease for further diagnostic inquiry based on the accumulated total weight.

31. The method defined in claim 23, additionally comprising providing a degree of certainty of ruling-in the disease.

32. The method defined in claim 23, additionally comprising ruling-out the disease for further diagnostic inquiry based on the accumulated total weight.

33. The method defined in claim 32, additionally comprising providing a degree of certainty of ruling-out the disease.

34. The method defined in claim 23, wherein repetitively asking questions comprises asking questions for diseases deemed urgent before questions for non-urgent diseases.

35. The method defined in claim 23, additionally comprising determining whether the accumulated total weight for a disease reaches or passes a rule-out threshold so as to eliminate a possible diagnosis.

36. The method defined in claim 23, additionally comprising accumulating a plurality of diagnoses, each diagnosis having a degree of certainty, into a patient specific differential diagnosis list.

37. The method defined in claim 23, wherein repetitively asking questions to elicit responses comprises repetitively asking questions to elicit responses from a patient.

38. The method defined in claim 23, wherein the weight contributed by an established symptom is a negative integer.

39. A computer usable medium having computer readable program code embodied therein for performing a computerized process used in medical diagnosis, the computer readable code comprising instructions for:
providing a list of diseases, each disease associated with a list of symptoms, and each symptom associated with a list of questions; and
executing a script engine comprising:
repetitively asking questions selected from the lists of questions to elicit responses from a patient;
establishing symptoms selected from the lists of symptoms based on the responses;
contributing a weight to an accumulated total weight for a disease selected from the lists of disease based on each established symptom; and
determining whether the accumulated total weight for a the selected disease reaches or passes a threshold so as to declare a diagnosis.

40. The computer usable medium of claim 39, additionally comprising instructions for accumulating a plurality of diagnoses, each diagnosis having a degree of certainty, into a patient specific differential diagnosis list.

41. The computer usable medium defined in claim 39, wherein the weight contributed by an established symptom is a negative integer.

42. A computerized medical diagnostic system, comprising:
a storage having a list of diseases, each disease associated with a list of symptoms, and each symptom associated with a list of questions; and
a storage having a script engine operating on a computer and configured to:
repetitively ask questions selected from the lists of questions to elicit responses from a patient, the responses establishing symptoms selected from the lists of symptoms, each established symptom contributing a weight to an accumulated total weight for a disease selected from the lists of disease, and
determine whether the accumulated total weight for a the selected disease reaches or passes a threshold so as to declare a diagnosis.

43. The system defined in claim 42, wherein the weight contributed by an established symptom is a negative integer.

44. The system defined in claim 42, wherein the storage having the list of diseases and the storage having the script engine are the same device.

* * * * *

UNITED STATES PATENT AND TRADEMARK OFFICE
CERTIFICATE OF CORRECTION

| | |
|---|---|
| PATENT NO. | : 7,344,496 B2 |
| APPLICATION NO. | : 10/656592 |
| DATED | : March 18, 2008 |
| INVENTOR(S) | : Edwin C. Iliff |

It is certified that error appears in the above-identified patent and that said Letters Patent is hereby corrected as shown below:

Title Page; item (56);

Page 2, Column 2 (Other Publications section), Line 29, delete "Frudenheim," and insert -- Frudenhelm, --, therefor.

Page 3, Column 2 (Other Publications section), Line 30, delete "weight-threshold" and insert -- weight/threshold --, therefor.

Sheet 16 of 20 (FIG. 11, Reference Character 622), Line 3, delete "SERVICES(S)" and insert -- SERVICE(S) --, therefor.

Sheet 20 of 20 (FIG. 15, Reference Character 782), Line 2, delete "BAASED" and insert -- BASED --, therefor.

Sheet 20 of 20 (FIG. 15, Reference Character 796), Line 2, delete "RESPONSSE" and insert -- RESPONSE --, therefor.

Column 3, Line 12, after "FIG." delete "3a;" and insert -- 3a --, therefor.

Column 9, Line 48 (approximately), after "symptoms" insert -- . --.

Column 14, Line 8, delete "smoked?)" and insert -- smoked?") --, therefor.

Column 28, Line 43, after "-10000" insert -- ) --.

Column 29, Line 50 (approximately), delete "containslists" and insert -- contains lists --, therefor.

Column 30, Line 22, delete "s_cfsnotinorder100" and insert -- s_cfsnotinorder 100 --, therefor.

Column 31, Line 14, delete "s_1bout other" and insert -- s_1bout_other --, therefor.

Column 31, Line 31, after "s_nosweats" delete "100" and insert -- –100 --, therefor.

Column 32, Line 48, delete "s_1bout1day" and insert -- s_1bout_1day --, therefor.

Signed and Sealed this

First Day of June, 2010

David J. Kappos
*Director of the United States Patent and Trademark Office*

CERTIFICATE OF CORRECTION (continued)
U.S. Pat. No. 7,344,496 B2

Column 33, Line 14, delete "t_kane" and insert -- t_kone --, therefor.

Column 33, Line 60, in Claim 1, delete "operating" and insert -- that operates --, therefor.

Column 33, Line 61, in Claim 1, after "and" insert -- is --.

Column 33, Line 67, in Claim 1, delete "lists" and insert -- list --, therefor.

Column 35, Line 20, in Claim 23, delete "lists of disease" and insert -- list of diseases --, therefor.

Column 35, Line 54, in Claim 31, delete "claim 23," and insert -- claim 30, --, therefor.

Column 36, Line 29, in Claim 39, delete "lists of disease" and insert -- list of diseases --, therefor.

Column 36, Line 31, in Claim 39, after "for" delete "a".

Column 36, Line 47 (approximately), in Claim 42, delete "operating" and insert -- that operates --, therefor.

Column 36, Line 48 (approximately), in Claim 42, after "and", insert -- is --.

Column 36, Line 54 (approximately), in Claim 42, delete "lists of disease," and insert -- list of diseases, --, therefor.

Column 36, Line 55 (approximately), in Claim 42, after "for" delete "a".